US006337328B1

(12) United States Patent
Fang et al.

(10) Patent No.: US 6,337,328 B1
(45) Date of Patent: *Jan. 8, 2002

(54) BUPROPION METABOLITES AND METHODS OF USE

(75) Inventors: Qun Kevin Fang, Wellesley; Chrisantha Hugh Senanayake, Shrewsbury; Paul Grover, Franklin, all of MA (US)

(73) Assignee: Sepracor, Inc., Marlborough, MA (US)

( * ) Notice: Subject to any disclaimer, the term of this patent is extended or adjusted under 35 U.S.C. 154(b) by 0 days.

(21) Appl. No.: 09/640,725

(22) Filed: Aug. 18, 2000

Related U.S. Application Data

(63) Continuation-in-part of application No. 09/510,241, filed on Feb. 22, 2000.
(60) Provisional application No. 60/148,324, filed on Aug. 11, 1999, and provisional application No. 60/122,277, filed on Mar. 1, 1999.

(51) Int. Cl.[7] ..................... A61K 31/535; A61K 31/135
(52) U.S. Cl. ..................... 514/231.2; 514/649; 514/653
(58) Field of Search ............................ 514/231.2, 649, 514/653

(56) References Cited

U.S. PATENT DOCUMENTS

| | | |
|---|---|---|
| 3,536,809 A | 10/1970 | Applezweig |
| 3,598,123 A | 8/1971 | Zaffaroni |
| 3,622,675 A | 11/1971 | Koppe et al. |
| 3,630,200 A | 12/1971 | Higuchi |
| 3,819,706 A | 6/1974 | Mehta |
| 3,845,770 A | 11/1974 | Theeuwes et al. |
| 3,885,046 A | 5/1975 | Mehta |
| 3,916,899 A | 11/1975 | Theeuwes et al. |
| 3,960,927 A | 6/1976 | Metcalf et al. |
| 4,008,719 A | 2/1977 | Theeuwes et al. |
| 4,347,176 A | 8/1982 | Mehta |
| 4,347,177 A | 8/1982 | Phillips |
| 4,347,178 A | 8/1982 | Findlay et al. |
| 4,347,257 A | 8/1982 | Stern |
| 4,347,382 A | 8/1982 | Scharver |
| 4,355,179 A | 10/1982 | Findlay et al. |
| 4,356,165 A | 10/1982 | Findlay et al. |
| 4,393,078 A | 7/1983 | Peck |
| 4,425,363 A | 1/1984 | Stern |
| 4,435,449 A | 3/1984 | Stern |
| 4,438,138 A | 3/1984 | Stern |
| 4,507,323 A | 3/1985 | Stern |
| 4,571,395 A | 2/1986 | Peck |
| 4,656,026 A | 4/1987 | Coffman et al. |
| 4,687,660 A | 8/1987 | Baker et al. |
| 4,769,027 A | 9/1988 | Baker et al. |
| 4,798,826 A | 1/1989 | Peck |
| 4,835,147 A | 5/1989 | Roberts |
| 4,868,344 A | 9/1989 | Brown |
| 4,895,845 A | 1/1990 | Seed |
| 4,935,429 A | 6/1990 | Dackis et al. |
| 4,935,439 A | 6/1990 | Kashman et al. |
| RE33,994 E | 7/1992 | Baker et al. |
| 5,217,987 A | 6/1993 | Berger |
| 5,358,970 A | 10/1994 | Ruff et al. |
| 5,427,798 A | 6/1995 | Ludwig et al. |
| 5,447,948 A | 9/1995 | Seibyl et al. |
| 5,512,593 A | 4/1996 | Dante |
| 5,541,231 A | 7/1996 | Ruff et al. |
| 5,731,000 A | 3/1998 | Ruff et al. |
| 5,753,712 A | 5/1998 | Pinsker |
| 5,763,493 A | 6/1998 | Ruff et al. |

FOREIGN PATENT DOCUMENTS

| | | |
|---|---|---|
| CA | 977777 | 11/1975 |
| CA | 977778 | 11/1975 |
| EP | 0 118 036 | 9/1984 |
| EP | 0 171 227 | 2/1986 |
| EP | 0 467 488 | 1/1992 |
| JP | 63-91352 | 4/1988 |
| WO | WO 91/11184 | 8/1991 |
| WO | WO 92/19226 | 11/1992 |
| WO | WO 93/21917 | 11/1993 |
| WO | WO 94/04138 | 3/1994 |
| WO | WO 94/20100 | 9/1994 |
| WO | WO 95/03791 | 2/1995 |
| WO | WO 95/22324 | 8/1995 |
| WO | WO 96/39133 | 12/1996 |
| WO | WO 97/29735 | 8/1997 |
| WO | WO 98/50044 | 11/1998 |
| WO | WO 99/37305 | 7/1999 |

OTHER PUBLICATIONS

Ascher, J.A. et al., 1995, "Bupropion: a review of its mechanism of antidepressant activity", J. Clin. Psych. 56:395–401.

Bannon et al., 1998, "Broad–spectrum, non–opoid analgesic activity by selective modulation of neuronal nicotinic acetylchroline receptors," Science 279:77–81.

Bischoff et al., 1984, "Affinity changes of rat striatal dopamine receptor in vivo after acute bupropion treatment", Eur. J. Pharmaco. 104:173–176.

Blondel–Hill et al., 1993, "Treatment of the chronic fatigue syndrome", Drugs 46(4):639–651.

Borowski, T.B. et al., 1993, "Amphetamine and antidepressant drug effects of GABA– and NMDA–related seizures", Brain Res. Bull. 30:607–610.

Calabrese, J.R. et al., 1991, "Treatment of depression", Primary Care 18(2):421–433.

Castaldi, G. et al., 1987, "Tataric acid, and efficient chiral auxillary: new asymmetric synthesis of 2–alkyl–2–arylacetic acids", J. Org. Chem. 52:3018.

Castello, R.A. and Mattocks, A.M., J. Pharm. Sci. 51(2):106–108 (1962).

Charney, D.S. et al 1983, "Monoamine receptor sensitivity and depression: clinical studies of antidepressant effects on serotonin and noradrenergic function," Psychopharmacol. Bull 19(3):490.

(List continued on next page.)

*Primary Examiner*—William R. A. Jarvis
(74) *Attorney, Agent, or Firm*—Pennie & Edmonds LLP

(57) ABSTRACT

Methods are disclosed which utilize metabolites of bupropion for treating sexual dysfunction.

94 Claims, 1 Drawing Sheet

OTHER PUBLICATIONS

Clay et al., 1988, "Clinical and neuropsychological effects of the novel antidepressant bupropion", Psychopharma. Bull. 24(1):143–148.

Conners, K.C. et al., 1996, "Bupropion hydrochloride in attention deficit disorder with hyperactivity", J. Am. Acad. Child Adolesc. Psychiatr. 34(10):1314–1321.

Cook C.E., 1997, "Therapeutic advances in the treatment of cigarette addiction", J. Pharmacy Practice 10(5):329–337.

Cooper, B.R. et al., 1994, "Evidence that the acute behavioral and electrophysiological effects of bupropion (Wellbutrin®) are mediated by an noradrenergic mechanism", Neuropsychopharmacology 11(2):133–141.

Cooper, T.B. et al., Analytical psychopharmacology: NY State Psychiatric Institute pp. 1–3, 1988.

Coutts, R.T. & Baker, G.B., 1989, "Implications of chirality and geometric isomerisms in some psychoactive drugs and their metabolites", Chirality 1:99–120.

Crenshaw et al., 1987, "Pharmacological modification of psychosexual dysfunction", J. Sex. Marital Ther. 13(4):239–252.

Cusack, B. et al., 1994, "Binding of antidepressants to human brain receptors: focus on newer generation compounds", Psychopharmacol. 114:559–565.

Davidson et al., 1994, "Bupropion in chronic low back pain", J. Clin. Psychiatry 55(8):362.

Dilsaver, S.C. et al., 1992, "The efficacy of bupropion in winter depression: results of an open trial", J. Clin. Psychiatry 53(7):252–255.

Eliel, E.L., 1962, *Stereochemistry of Carbon Compounds*, McGraw–Hill, NY.

Ferris, R.M. et al., 1983, "Studies of bupropion's mechanism of antidepressant activity", J. Clin. Psychiatry 44(5):74–78.

Ferris & Beaman, 1983, "Bupropion: a new antidepressant drug, the mechanism of action of which is not associated with down–regulation of postsynaptic β–adrenergic, serotonergic (5–HT$_2$), α$_2$–adrenergic, imipramine and dopaminergic receptors in brain", Neuropharmacol. 22(1):1257–1267.

Ferry, L.H. et al, 1992, "Enhancement of smoking cessation using the anti–depressant bupropion hydrochloride" (abstract) Circulation 86:671.

Ferry, L.H. et al., 1994, "Efficacy of bupropion for smoking cessation in non–depressed smokers," J. Addict, Dis. 13:A9.

Fisher, R.S., 1989, "Animal models of the epilepsies", Brain Res. Reviews 14:245–278.

Foote et al., 1984, "Proconvulsant effect of morphine on seizures induced by pentylenetetrazol in the rat", 105:179–184.

Garland et al., 1998, "Pharmacotherapy of adolescent attention deficit hyperactivity disorder: challenges, choices and caveats", J. Psychopharmacology 12(4):385–395.

Goetz et al., 1984, "Bupropion in Parkinson's Disease," 34:1092–4.

Goodnick, P.J., 1994, "Pharmacokinetic optimisation of therapy with newer antidepressants", Clin. Pharmacokinet. 27(4):307–330.

Goodnick, P.J. & Sandoval, R., 1993, "Psychotropic treatment of depression: results of an open trial", J. Clin. Psych. 54(1):13–20.

Green, A.R. & Murray, T.K., 1989, "A simple intravenous infusion method in rodents for determining the potency of anticonvulsants acting through GABAergic mechanisms", J. Pharm. Pharmacol. 41:879–880.

Grimes et al., 1996, "Spontaneous orgasm with the combined use of bupropion and serttaline", Soc. Biol. Psych. 40:1184–1185.

Handbook of Pharmaceutical Excipients, 2nd ed., Wade and Willer eds., pp. 257–259 (1994).

Hsyu, P.H. et al., 1997, "Pharmacokinetics of bupropion and its metabolites in cigarette smokers versus nonsmokers", J. Clin. Pharmacol. 37(8):737–743.

Hsyu, P.H. et al., Nov. 10, 1997 Chemical Abstracts 127(19): Abstract No. 257089; Columbus, Ohio.

Janowsky, A., et al., J. Neurochem. 46:1272–1276 (1986).

Kelley, J.L. et al., 1996, "(2S,3S,5R)–2–(3,5,–difluorophenyl)–3,5–dimethyl–2–morpholinol: a novel antidepressant agent and selective inhibitor of norepinephrine uptake", J. Med. Chem. 39:347–349.

Ketter, T.A. et al., 1995, "Carbamazepine but not valproate induces bupropion metabolism", J. Clin. Psychopharmacol. 15(5):327–333.

Laizure, S.C. et al., 1985, "Pharmacokinetics of bupropion and its major basic metabolites in normal subjects after a single dose", Clin. Pharmacol. Ther. 38:586–589.

Lief, H.I., 1996, "Bupropion treatment of depression to assit smoking cessation", Am. J. Psychiatry 153(3):442.

Little, K.Y. et al., 1993, "[$^{125}$I]RTI–55 binding to cocaine–sensitive dopaminergic and serotonergic uptake sites in the human brain", J. Neurochem. 61:1996–2006.

Martin, P, et al., 1990, "Antidepressant Profile of Bupropion and Three Metabolites in Mice," Pharmacopsychiatry 23:187–194.

McNamee et al., 1986, "Stimulation of substrate oxidation in rat hepatic mitochondria following pretreatment with apetite modifying drugs", J. Pharm. Pharmacol. 37:147.

Merskey, H., 1965, "The effect of chronic pain upon the response to noxious stimuli by psychiatric patients," J. Psychosom. Res. 8:405–419.

Michell, G.F. et al., 1989, "Effect of bupropion on chocolate craving", Am. J. Psychiatry 146(1):119–120.

Michell, G.F. et al., 1989, "Dr, Mitchell and associates reply", Am. J. Psychiatry 146(8):1089.

Moisset, B., et al., Brain Res. 92:157–164 (1975).

Moret, C. & Brile, M., 1988, "Sensitizing of the response of 5–HT autoreceptors to drugs modifying synaptic availability of 5–HT", 27(1):43–49.

Musso et al., 1993, "Synthesis and evaluation of the antidepressant activity of the enantiomers of bupropion", Chirality 5:495–500.

Musso et al., 1997, "Synthesis and Evaluation of the Anticonvulsant Activity of a Series of 2–Amino–Phenyl–1–Propanols Derived from the Metabolites of the Antidepressant Bupropion," Bioorganic & Medical Chemistry Letters, vol. 7 No. 1, pp. 1–6, 1997.

Neurology, Official Journal of American Academy of Neurology, Aug. 1984, vol. 34, No. 8.

Nomikos et al., 1992, "Effects of chronic bupronion on interstitial concentrations of dopamine in rat nucleus accumbens and straitum", Neuropsychopharmacology 7(1):7–14.

Nutt, D.J. et al., 1981, "Studies on the postietal rise in seizure threshold," Eur. J. Pharmacol. 71:287–295.

Nutt, D.J. Et al, 1980, "On the measurement in rats of the convulsant effect of drugs and the changes which follow electronconvulsive shock," *Neuropharmacology* 19:1017–1023.

Olsen et al., 1985, "Benzodiazepine/γ–aminobutyric acid receptor deficit in the midbrain of the seizure–susceptible gerbil", PNAS USA 82:6701–6705.

Pearlstein et al., 1997, "Comparison of fluoxetine, bupropion, and placebo in the treatment of premenstrual dysphoric disorder", J. Clin. Psychopharmacol. 17(4):261–266.

Physician's Desk Reference®, 1998, pp. 1120–1127.

Popli, A.P. et al., 1994, "Antidepressant–associated seizures", J. Clin. Psych. 55(6):267.

Popli, A. et al., 1995, "Bupropion and anticonvulsant drug interactions", Annals of Clin. Psychiatr. 7(2):99–101.

Posner, J. et al., 1985, "The disposition of bupropion and its metabolites in healthy male volunteers after single and multiple doses", Eur. J. Clin. Pharmacol. 29:97–103.

Potter, W.Z. & Manji, H.K., 1990, "Antidepressants, metabolites, and apparent drug resistance", Clin. Neuropharmacol. 13(1):S45–S53.

Remingtons: The Practice of the Science and Pharmacy, 19th ed., Gennaro, eds., p. 1625 (1995).

Rose, J.E., 1996, "Nicotine addiction and treatment", Annu. Rev. Med. 47:493–507.

Rosenstein, D.L. et al., 1993, "Seizure associated with antidepressants: a review", J. Clin. Psychiatry 54(8):289–299.

Rudorfer, M.V. et al., 1994, "Comparative tolerability profiles of the newer versus older antidepressants", Drug Safety 10(1):18–46.

Schroeder, D.H., 1983, "Metabolism and kinetics of bupropion", J. Clin. Psychiatr. 44(5):79–81.

Schroedger, D.H. et al., 1979, "The isolation and identification of some basic urinary metablites of bupropion—HCL in man", The Pharmacologist 21(3):191.

Scrip Bupropion Sustained Release (SR) for Smoking Cessation, Dec. 18, 1996.

Scrip Itraconazole for pulse dosing of onychomycosis, Dec. 18, 1996.

Scrip's New Product Review, No. 50 Bupropion, PJB Publications: United Kingsome, Aug., 1990.

Stathis, M. et al., 1995 , "Rate of binding of various inhibitors at the dopamine transporter in vivo", Psychopharmacol. 119:376–384.

Storrow, A.B., 1994, "Bupropion overdose and seizure", Am. J. Emerg. Med. 12:183–184.

Suckow, R.F. et al., 1986, "Pharmacokinetics of bupropion and metabolites in plasma and brain of rats, mice, and guinea pigs", Drug Metab. Disposit. 14(6):692–697.

Suckrow, R.F. et al., 1997, "Enantiomeric determination of the phenylmorpholine metabolite of bupropion in human plasma using coupled achiral–chiral liquid chromatography", Biomedical Chromatog. 11:174–179.

Sulser, F., 1983, "Molecular mechanisms in antidepressant action," *Psychopharmacol. Bull.* 19(3):300.

Sweet, R.A. et al., 1995, "Pharmacokinetics of single–and multiple–dose bupropion in elderly patients with depression", J. Clin. Pharmacol. 35:876–884.

Testa B. and Trager, W.F., 1990, "Racemates Versus Enantiomers in Drug Development: Dogmatism or Pragmatism?" Chirality 2:129–133.

Vassout, A. et al., 1993, "Regulation of dopamine receptors by bupropion: comparison with antidepressants and CNS stimulants", J. Receptor Res. 13(1–4):341–354.

Ward, N.G., 1990, *The Management of Pain*, Second Edition, vol. 1, Chapter 18 (eds.) Bonica, J.J. pp. 310–319.

Ward, R. et al., 1971, "Asymmetric audiogenic seizures in mice: a possible analogue of focal epilepsy", Brain Res. 31:207–210.

Welch, R.M. et al., 1987, "Pharmacological significance of the species differences in buporopion metabolism", Nenobiotica 17(3):287–298.

Wilen, S.H., 1972, *Tables of Resolving Agents and Optical Resolutions*, Univ. of Notre Dame Press, Notre Dame, IN.

Wright et al., 1985, "Bupropion in the long–term treatment of cyclic mood disorders: mood stabilizing effects", J. Clin. Psych. 46(1):22–25.

Zarrindast et al., 1988, "Anorectic and behavioral effects of bupropion", Gen. Pharmacology 19(2):201–204.

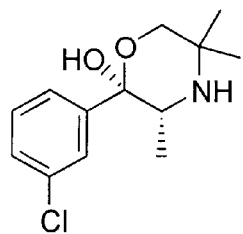

(R,R)-2-(3-Chlorophenyl)-2-
hydroxy-3,5,5-trimethyl-morphinol

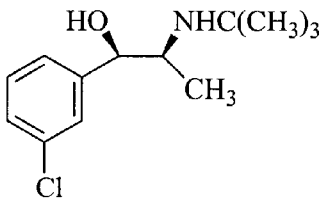

(R,S)-2-(tert-Butylamino)-1-
(3-chlorophenyl)-propan-1-ol

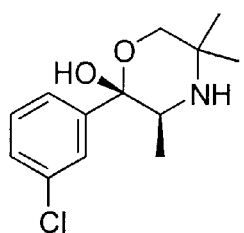

(S,S)-2-(3-Chlorophenyl)-2-
hydroxy-3,5,5-trimethyl-morphinol

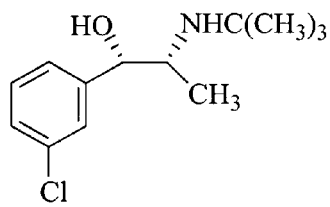

(S,R)-2-(tert-Butylamino)-1-
(3-chlorophenyl)-propan-1-ol

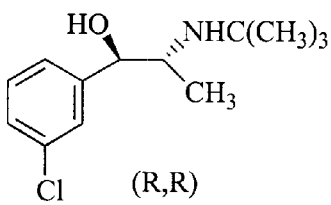

(R,R)-2-(tert-Butylamino)-1-
(3-chlorophenyl)-propan-1-ol

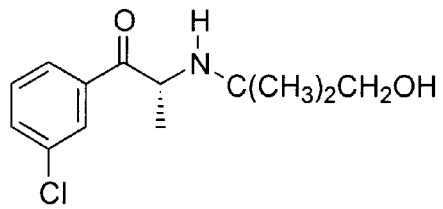

(R)-1-(3-Chlorophenyl)-2-[(1,1-
dimethylethanol)amino]-1-propanone

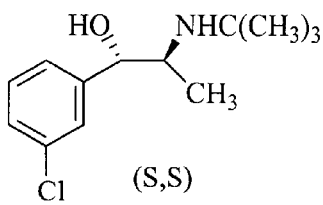

(S,S)-2-(tert-Butylamino)-1-
(3-chlorophenyl)-propan-1-ol

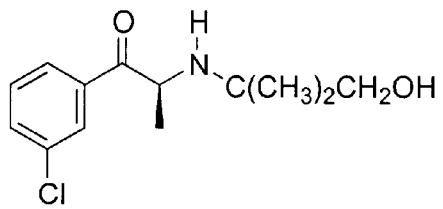

(S)-1-(3-Chlorophenyl)-2-[(1,1-
dimethylethanol)amino]-1-propanone

FIGURE 1

BUPROPION METABOLITES AND METHODS OF USE

This application is a continuation-in-part of copending application Ser. No. 09/510,241, filed Feb. 22, 2000, which claims priority to provisional application no. 60/148,324, filed Aug. 11, 1999, and provisional application no. 60/122,277, filed Mar. 1, 1999, each of which is incorporated herein by reference.

1. FIELD OF THE INVENTION

This invention relates to the synthesis of, methods of using, and compositions comprising bupropion metabolites, their isomers, and salts thereof.

2. BACKGROUND OF THE INVENTION

Bupropion, a racemic mixture of (+)- and (−)-1-(3-chlorophenyl)-2-[(1,1-dimethylethyl)amino]-1-propanone, is an antidepressant of the aminoketone class, which is described in U.S. Pat. Nos. 3,819,706 and 3,885,046. The hydrochloride salt of bupropion is sold under the tradenames WELLBUTRIN® and WELLBUTRIN SR® (Glaxo Wellcome Inc.) for the treatment of depression. Bupropion is also sold under the tradename ZYBAN® (Glaxo Wellcome Inc.) as a drug useful to achieve smoking cessation. Additional benefits of bupropion maleate are reported in European Patent Application No. 118036.

Although its mechanism of action is poorly understood, bupropion is reportedly a weak but selective inhibitor of dopamine. Its potency as an inhibitor of norepinephrine reuptake is reportedly only half of that for dopamine, and it shows little affinity for the serotonergic transport system. Ascher, J. A., et al., *J Clin. Psychiatry*, 56:395–401 (1995).

Bupropion is extensively metabolized in man and animal. Three metabolites found in the plasma of healthy humans to whom it has been administered are shown in Scheme 1:

Posner, J., et al., *Eur. J. Clin Pharmacal.*, 29:97–103 (1985); Suckow, R. F., et al., *Biomedical Chromatography*, 11:174–179 (1997). Referring to Scheme 1, metabolite 1 has the chemical name 2-(3-chlorophenyl)-2-hydroxy-3,5,5-trimethyl-morpholinol; metabolite 2 has the chemical name 2-(tert-butylamino)-1-(3-chlorophenyl)-propane-1-ol; and metabolite 3 has the chemical name 1-(3-chlorophenyl)-2-[(1,1-dimethylethanol)amino]-1-propanone. Because bupropion is administered as a racemate and its metabolites are chiral, stereomeric mixtures of each of the metabolites 1, 2, and 3 likely exist in human plasma following its administration.

The bupropion metabolite 1, often referred to as "hydroxybupropion," has two chiral carbon atoms and can thus theoretically exist as two pairs of enantiomers. These are shown in Scheme 2:

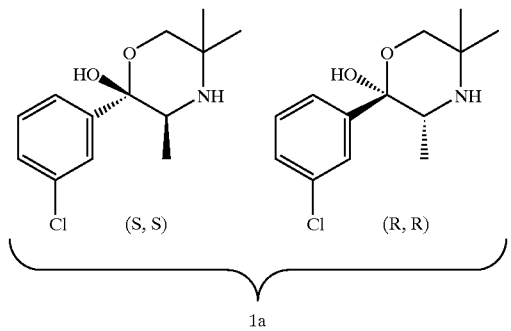

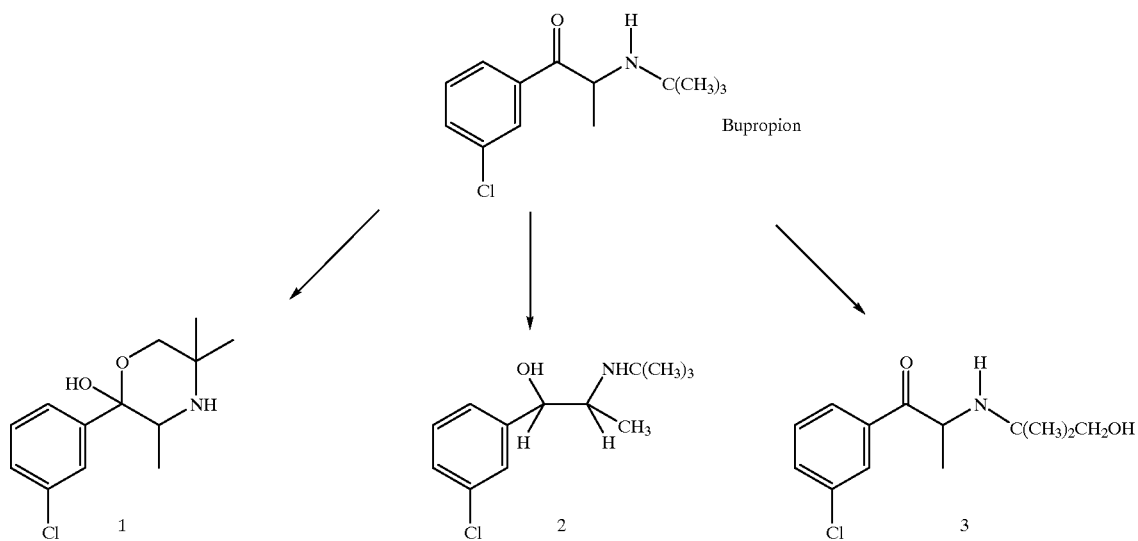

-continued

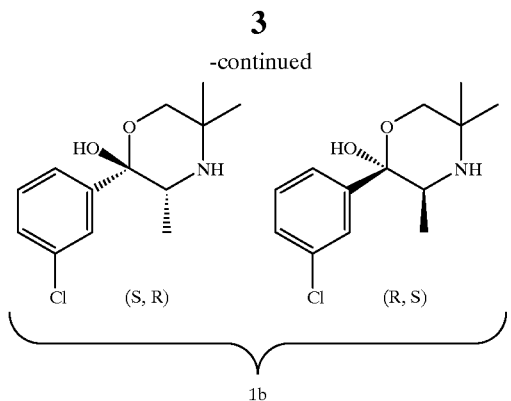

1b

Based on studies using racemic bupropion in mice, it has been suggested that racemic hydroxybupropion may contribute to the antidepressant profile of racemic bupropion in depressed patients. Kelley, J. L., et al., *J. Med. Chem.*, 39:347–349 (1996). The mixture 1a has been isolated from human plasma and allegedly separated into its (S,S) and (R,R) components. Suckow, R. F., et al., *Biomedical Chromatography*, 11:174–179 (1997). However, activity of the individual enantiomers was not reported in Suckow.

The amino alcohol metabolite 2, also referred to as "dihydrobupropion," can also exist as two pairs of enantiomers. These are shown in Scheme 3:

Scheme 3

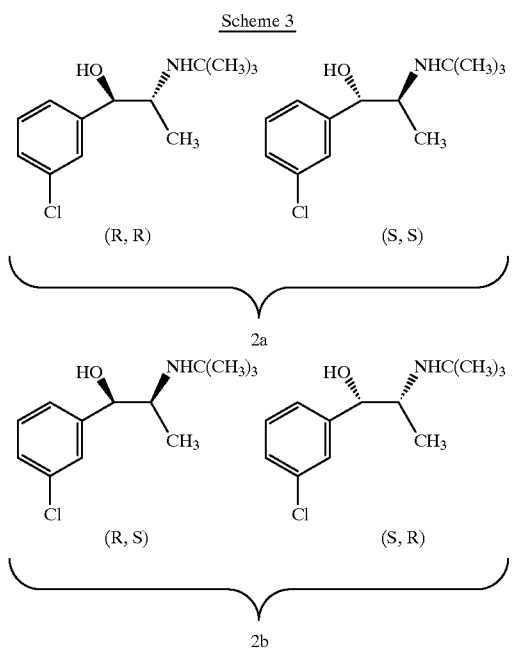

The pair wherein the alcohol and amine moieties are cis to each other is commonly referred to as the erythro-amino alcohol metabolite; the pair wherein the two moieties are trans to each other is referred to as the threo-amino alcohol metabolite.

The tert-butyl alcohol metabolite 3 can exist as one of two enantiomers. This racemic metabolite, the accumulation of which in human plasma coincides with the elimination of a single dose of bupropion, is believed by some to be a precursor to hydroxybupropion. Posner, J., et al., *Eur. J. Clin. Pharmacol.*, 29:97–103 (1985); Suckow, R. F., et al., Biomedical Chromatography, 11: 174–179 (1997).

Clearly, the metabolism of bupropion, which is complicated and poorly understood, results in a complex array of chiral compounds. The structures of these molecules and their chirality provide the skilled artisan with difficult issues of asymmetric synthesis, chiral resolution, and pharmacological activity.

Racemic bupropion is widely used to treat affective disorders in patients who do not respond to, or cannot tolerate, other antidepressants such as tricyclic agents or monoamine oxidase inhibitors. Examples of affective disorders are depression and bipolar manic-depression. Racemic bupropion is also useful in the treatment of other diseases or conditions associated with the reuptake of neuronal monoamines such as serotonin and norepinephrine. These reportedly include: schizophrenia (U.S. Pat. No. 5,447,948); attention-deficit disorder; psycho-sexual dysfunction (U.S. Pat. No. 4,507,323); bulimia and other eating disorders; Parkinson's disease; migraine (U.S. Pat. No. 5,753,712); and chronic pain. Racemic bupropion also reportedly increases success rates in some smoking cessation treatments. Rose, J. E., *Annu. Rev. Med.*, 47:493–507 (1996); Ferry, L. H. et al., *J. Addict. Dis.*, 13:A9 (1994); and Lief, H. I., *Am. J. Psychiatry*, 153(3):442 (1996).

Further uses of racemic bupropion reportedly include the treatment of: the effects of ethanol (U.S. Pat. No. 4,393,078); tardive dyskinesia (U.S. Pat. No. 4,425,363); drowsiness (U.S. Pat. Nos. 4,571,395 and 4,798,826); minimal brain dysfunction (U.S. Pat. No. 4,435,449); psychosexual dysfunction (U.S. Pat. No. 4,507,323); prostate hypertrophy and sexual dysfunction (U.S. Pat. No. 4,835,147); psychostimulant addiction (U.S. Pat. No. 4,935,429); substance abuse (U.S. Pat. No. 5,217,987); high cholesterol (U.S. Pat. No. 4,438,138); and weight gain (U.S. Pat. No. 4,895,845).

Certain advantages exist in using bupropion for the treatment of diseases and conditions. For example, bupropion does not inhibit monoamine oxidase or block the reuptake of serotonin, unlike other neuronal monoamine reuptake inhibitors. Administration of bupropion can thus avoid or lessen many adverse effects commonly associated with other antidepressants such as tricyclic agents and monoamine oxidase inhibitors.

Unfortunately, racemic bupropion is not free of adverse effects. Administration of the drug can cause seizures, especially in patients currently taking the monoamine oxidase inhibitor phenelzine. Other frequently reported adverse effects associated with the use of racemic bupropion include nausea, vomiting, excitement, agitation, blurred or blurry vision, restlessness, postural tremors, hallucinations/confusional states with the potential for abuse, anxiety, insomnia, headaches and/or migraines, dry mouth, constipation, tremor, seizures, sleeping disturbances, dermatologic problems (e.g., rashes), neuropsychiatric signs and symptoms (e.g. delusions and paranoia), and weight loss or gain. See, e.g., *Physicians' Desk Reference®* 1252–1258 ($53^{rd}$ ed. 1999). These effects are dose limiting in a number of patients, and can be particularly dangerous for Parkinson's patients.

Thus, there remains a need for a drug that provides the advantages of racemic bupropion, but with fewer disadvantages. Compounds and pharmaceutical compositions are desired that can be used for the treatment and prevention of disorders and conditions while reducing or avoiding adverse effects associated with the administration of racemic bupropion.

3. SUMMARY OF THE INVENTION

This invention encompasses methods of making and using bupropion metabolites and pharmaceutically acceptable salts, solvates, hydrates, and clathrates thereof, and pharmaceutical compositions and dosage forms comprising bupropion metabolites and pharmaceutically acceptable salts, solvates, hydrates, and clathrates thereof. In particular, the invention provides methods of synthesizing optically pure (S,S)-hydroxybupropion, and optically pure (R,R)-hydroxybupropion. In addition, the invention encompasses methods of synthesizing optically pure (S,S)-dihydrobupropion, (R,R)-dihydrobupropion, (S,R)-dihydrobupropion, and (R,S)-dihydrobupropion.

The invention further provides methods of treating and preventing conditions that include, but are not limited to, sexual dysfunction, affective disorders, cerebral function disorders, substance addiction, tobacco smoking, and incontinence. Methods of the invention comprise administering to a patient in need of such treatment or prevention, a therapeutically or prophylactically effective amount of a bupropion metabolite, or a pharmaceutically acceptable salt, solvate, hydrate, or clathrate thereof. Additional methods of the invention further comprise the use of at least one additional physiologically active agent such as a selective serotonin reuptake inhibitor ("SSRI"), 5-$HT_3$ antagonist, or nicotine with a bupropion metabolite of the invention.

Pharmaceutical compositions and dosage forms of the invention comprise a therapeutically or prophylactically effective amount of a bupropion metabolite or a pharmaceutically acceptable salt, solvate, hydrate, or clathrate thereof, and optionally at least one additional physiologically active agent such as a SSRI, 5-$HT_3$ antagonist, or nicotine.

3.1. DEFINITIONS

As used herein, the term "patient" includes mammals, and preferably humans.

As used herein, the tern "bupropion metabolite" includes, but is not limited to, racemic and optically pure forms of 2-(3-chlorophenyl)-2-hydroxy-3,5,5-trimethyl-morpholinol (also known as hydroxybupropion), 2-(tert-butylamino)-1-(3-chlorophenyl)-propan-1-ol (also known as dihydrobupropion), and 1-(3-chlorophenyl)-2-[(1,1-dimethylethanol)amino]-1-propanone. As used herein, the term "optically pure bupropion metabolite" includes, but is not limited to, optically pure: (R,R)-2-(3-chlorophenyl)-2-hydroxy-3,5,5-trimethyl-morpholinol (also called (R,R)-hydroxybupropion); (S,S)-2-(3-chlorophenyl)-2-hydroxy-3,5,5-trimethyl-morpholinol (also called (S,S)-hydroxybupropion); (R,R)-2-(tert-butylamino)-1-(3-chlorophenyl)-propan-1-ol (also called (R,R)-dihydrobupropion); (S,R)-2-(tert-butylamino)-1-(3-chlorophenyl)-propan-1-ol (also called (S,R)-dihydrobupropion); (S,S)-2-(tert-butylamino)-1-(3-chlorophenyl)-propan-1-ol (also called (S,S)-dihydrobupropion); (R,S)-2-(tert-butylamino)-1-(3-chlorophenyl)-propan-1-ol (also called (R,S)-dihydrobupropion); (R)-1-(3-chlorophenyl)-2-[(1,1-dimethyl-ethanol)amino]-1-propanone; and (S)-1-(3-chlorophenyl)-2-[(1,1-dimethylethanol)amino]-1-propanone.

As used herein to describe a compound, the terms "substantially optically pure," "optically pure," "optically pure enantiomer," and "stereomerically pure" mean that the compound contains greater than about 90% of the desired stereoisomer by weight, preferably greater than about 95% of the desired stereoisomer by weight, and most preferably greater than about 99% of the desired stereoisomer by weight, said weight percent based upon the total weight of the stereoisomer(s) of the compound. As used herein to describe a compound, the term "substantially free" means that the compound contains less than about 10% by weight, preferably less than about 5% by weight, and more preferably less than about 1% by weight of the undesired stereoisomer(s).

As used herein, the term "adjunctively administered" refers to the administration of one or more compounds in addition to a bupropion metabolite, either simultaneously with the bupropion metabolite or at intervals prior to, during, or following administration of the bupropion metabolite to achieve the desired therapeutic or prophylactic effect.

As used herein, the terms "diastereomers" and "diastereomeric" refer to stereoisomers having distinct three-dimensional orientations that are not enantiomers. In particular these terms refer to compounds having two or more chiral centers.

As used herein, the term "stereoisomers" refers to compounds possessing at least one chiral center, i.e., compounds containing at least one carbon atom having four different groups attached thereto.

As used herein, the term "pharmaceutically acceptable salt" refers to a salt prepared from a pharmaceutically acceptable non-toxic inorganic or organic acid or base. The compounds of the invention that are basic in nature are capable of forming a wide variety of salts with various inorganic and organic acids. Acids that can be used to prepare pharmaceutically acceptable acid addition salts of such basic compounds of the invention are those that form non-toxic acid addition salts, i.e., salts containing pharmacologically acceptable anions, such as, but not limited to, hydrochloride, hydrobromide, hydroiodide, nitrate, sulfate, bisulfate, phosphate, acid phosphate, formate, acetate, propionate, succinate, camphorsulfonate, citrate, acid citrate, fumarate, gluconate, isothionate, lactate, malate, mucate, gentisate, isonicotinate, saccharate, tartrate, bitartrate, para-toluenesulfonate, glycolate, glucuronate, maleate, furoate, glutamate, ascorbate, benzoate, anthranilate, salicylate, phentylacetate, mandelate, embonate (pamoate), methanesulfonate, ethanesulfonate, pantothenate, benzenesulfonate, stearate, sulfanilate, alginate, p-toluenesulfonate, and galacturonate. Particularly preferred anions are hydrobromide, hydrochloride, phosphate, acid phosphate, maleate, sulfate, and acid phosphate. Most preferred anions are hydrochloride and maleate.

Compounds of the invention that are acidic in nature are capable of forming salts with various phannaceutically acceptable bases. The bases that can be used to prepare pharmaceutically acceptable base addition salts of such acidic compounds of the invention are those that form non-toxic base addition salts, i.e., salts containing pharmacologically acceptable cations such as, but not limited to, alkali metal or alkaline earth metal salts and the calcium, magnesium, sodium or potassium salts in particular. Suitable organic bases include, but are not limited to, N,N-dibenzylethylenediamine, chloroprocaine, choline, diethanolamine, ethylenediamine, meglumaine (N-methylglucamine), lysine, and procaine.

As used herein, the terms "avoiding adverse effects" and "avoiding adverse effects" mean eliminating or reducing at least one adverse effect associated with the administration of a particular compound or mixture of compounds.

As used herein, the term "adverse effects associated with racemic bupropion" includes, but is not limited to, seizures, nausea, vomiting, excitement, agitation, blurred or blurry vision, restlessness, postural tremors, hallucinations/confusional states with the potential for abuse, anxiety, insomnia, headaches and/or migraines, dry mouth, constipation, tremors, sleeping disturbances, dermatologic problems (e.g., rashes), neuropsychiatric signs and symptoms (e.g., delusions and paranoia), and weight gain.

As used herein, the term "adverse effects associated with the inhibition of dopamine reuptake" includes, but is not limited to, seizures, nausea, vomiting, excitement, agitation, blurred or blurry vision, restlessness, postural tremors, hallucinations/confusional states with the potential for abuse, anxiety, insomnia, headaches and/or migraines, dry mouth, constipation, tremor, sleeping disturbances, dermatologic problems (e.g., rashes), neuropsychiatric signs and symptoms (e.g., delusions and paranoia), and weight gain.

As used herein, the terms "disorder ameliorated by the inhibition of neuronal monoamine reuptake" and "disorder related to reuptake of neuronal monoamines" mean an acute or chronic disease, disorder, or condition having symptoms that are reduced or alleviated by the inhibition of neuronal monoamine reuptake, and especially by the inhibition of norepinephrine (or noradrenaline) and serotonin reuptake. Disorders ameliorated by inhibition of neuronal monoamine reuptake include, but are not limited to, erectile dysfunction, affective disorders, cerebral function disorders, tobacco smoking, and incontinence.

As used herein, the term "affective disorder" includes, but is not limited to, depression, anxiety disorders, attention deficit disorder, attention deficit disorder with hyperactivity, bipolar and manic conditions, bulimia, obesity or weight-gain, narcolepsy, chronic fatigue syndrome, seasonal affective disorder, premenstrual syndrome, substance addiction or abuse, and nicotine addiction.

As used herein, the term "substance addiction" includes, but is not limited to, addiction to cocaine, heroin, nicotine, alcohol, opioids, anxiolytic and hypnotic drugs, cannabis (marijuana), amphetamines, hallucinogens, phencyclidine, volatile solvents, and volatile nitrites. Nicotine addiction includes nicotine addiction of all known forms, such as smoking cigarettes, cigars and/or pipes, and addiction to chewing tobacco.

As used herein, the terms "attention deficit disorder" (ADD), "attention deficit disorder with hyperactivity" (ADDH), and "attention deficit/hyperactivity disorder" (AD/HD), are used in accordance with their accepted meanings in the art. See, e.g., *Diagniostic and Statistical Manual of Mental Disorders*, Fourth Ed., *American Psychiatric Association*, 1997 (DSM-IV™) and *Diagnostic and Statistical Manual of Mental Disorders*, $3^{rd}$ Ed., American Psychiatric Association (1981) (DSM-III™).

As used herein, the term "depression" includes a disease or condition characterized by changes in mood, feelings of intense sadness, despair, mental slowing, loss of concentration, pessimistic worry, agitation, and self-deprecation. Physical symptoms of depression that may be reduced or alleviated by the methods of the invention include insomnia, anorexia, weight loss, decreased energy and libido, and abnonnal hormonal circadian rhythms.

As used herein, the term "cerebral function disorder" includes, but is not limited to, disorders involving intellectual deficits such as senile dementia, Alzheimer's type dementia, memory loss, amnesia/amnestic syndrome, epilepsy, disturbances of consciousness, coma, lowering of attention, speech disorders, Parkinson's disease, Lennox syndrome, autistic disorder, autism, hyperkinetic syndrome and schizophrenia. Also within the meaning of the term are disorders caused by cerebrovascular diseases including, but not limited to, cerebral infarction, cerebral bleeding, cerebral arteriosclerosis, cerebral venous thrombosis, head injuries, and the like where symptoms include disturbance of consciousness, senile dementia, coma, lowering of attention, and speech disorders.

As used herein, the term "method of treating Parkinson's disease" means relief from the symptoms of Parkinson's disease which include, but are not limited to, slowly increasing disability in purposeful movement, tremors, bradykinesia, rigidity, and a disturbance of posture.

As used herein, the tern "sexual dysfunction" encompasses sexual dysfunction in men and women caused by psychological and/or physiological factors. Examples of sexual dysfunction include, but are not limited to, erectile dysfunction, premature ejaculation, vaginal dryness, vaginismus, decreased libido, lack of sexual excitement, anorgasmia, or inability to obtain orgasm. The term "sexual dysfunction" further encompasses psycho-sexual dysfunction. Examples of psycho-sexual dysfunction include, but are not limited to, inhibited sexual desire, inhibited sexual excitement, inhibited female orgasm, inhibited male orgasm, premature ejaculation, functional dyspareunia, functional vaginismus, and atypical psychosexual dysfunction.

As used herein, the term "method of treating or preventing sexual dysfunction" means prevention of, or relief from, sexual dysfunction or one or more symptoms of sexual dysfunction.

As used herein, the term "method of treating or preventing psycho-sexual dysfunction" means prevention of, or relief from, a symptom of inhibited sexual desire, inhibited sexual excitement, inhibited female orgasm, inhibited male orgasm, premature ejaculation, functional dyspareunia, functional vaginismus, and atypical psychosexual dysfunction.

As used herein, the term "a method for treating obesity or weight gain" means reduction of weight, relief from being overweight, relief from gaining weight, or relief from obesity, all of which are usually due to extensive consumption of food.

As used herein, the term "a method of treating or preventing incontinence" means prevention of or relief from the symptoms of incontinence including involuntary voiding of feces or urine, and dribbling or leakage of feces or urine which may be due to one or more causes including, but not limited to, pathology altering sphincter control, loss of cognitive function, overdistention of the bladder, hyper-reflexia and/or involuntary urethral relaxation, weakness of the muscles associated with the bladder, or neurologic abnormalities. As used herein, the term "urinary incontinence" encompasses stress urinary incontinence and urge urinary incontinence.

3.2. BRIEF DESCRIPTION OF THE DRAWINGS

Novel aspects of the invention can be better understood with reference to the figure described below:

FIG. 1 illustrates the chemical structures of compounds of the invention.

4. DETAILED DESCRIPTION OF THE INVENTION

This invention relates to the preparation of bupropion metabolites, particularly optically pure metabolites, and pharmaceutically acceptable salts, solvates, hydrates, and clathrates thereof, and their use to treat or prevent a variety of diseases or conditions in mammals and humans in particular. For example the invention encompasses methods and compositions that inhibit the reuptake of neuronal monoamines (e.g., norepinephrine). The invention thereby provides methods, pharmaceutical compositions, and dosage forms for the treatment or prevention of disorders that are ameliorated by the inhibition of neuronal monoamine reuptake including, but not limited to, sexual dysfunction, affective disorders, cerebral function disorders, substance addiction, tobacco smoking, narcolepsy, and incontinence.

The methods, pharmaceutical compositions, and dosage forms of the invention comprise a bupropion metabolite, or a pharmaceutically acceptable salt, solvate, hydrate or clathrate thereof. Preferred bupropion metabolite are optically pure. Specific preferred bupropion metabolites include optically pure (S,S)-hydroxybupropion (i.e., (S,S)-2-(3-chlorophenyl)-2-hydroxy-3,5,5-trimethyl-morpholinol), and (R,R)-hydroxybupropion (i.e., (R,R)-2-(3-chlorophenyl)-2-hydroxy-3,5,5-trimethyl-morpholinol). Other specific preferred bupropion metabolites include (RS,RS)-hydroxybupropion (i.e., (RS,RS)-2-(3-chlorophenyl)-2-hydroxy-3,5,5-trimethyl-morpholinol); (RS,RS)-dihydrobupropion (i.e., (RS,RS)-2-(tert-butylamino)-1-(3-chlorophenyl)-propan-1-ol); (R,R)-dihydrobupropion (i.e., (R,R)-2-(tert-butylamino)-1-(3-chlorophenyl)-propan-1-ol); (S,R)-dihydrobupropion (i.e., (S,R)-2-(tert-butylamino)-1-(3-chlorophenyl)-propan-1-ol); (S,S)-dihydrobupropion (i.e., (S,S)-2-(tert-butylamino)-1-(3-chlorophenyl)-propan-1-ol); (R,S)-dihydrobupropion (i.e., (R,S)-2-(tert-butylamino)-1-(3-chlorophenyl)-propan-1-ol); (RS)-1-(3-chlorophenyl)-2-[(1,1-dimethylethanol)amino]-1-propanone; (R)-1-(3-chlorophenyl)-2-[(1,1-dimethylethanol)amino]-1-propanone; and (S)-1-(3-chlorophenyl)-2-[(1,1-dimethylethanol)amino]-1-propanone.

A particularly preferred bupropion metabolite is (S,S)-hydroxybupropion, which is an unexpectedly selective norepinephrine reuptake inhibitor that does not significantly inhibit dopamine reuptake. It can thus be used to treat or prevent disorders related to norepinephrine reuptake without incurring adverse effects associated with the inhibition of dopamine reuptake. It can also be used to treat or prevent disorders related to norepinephrine reuptake while reducing or avoiding adverse effects associated with racemic bupropion.

A first embodiment of the invention encompasses a method of treating or preventing a disorder that is ameliorated by the inhibition of neuronal monoamine reuptake which comprises administering to a patient in need of such treatment or prevention a therapeutically or prophylactically effective amount of a bupropion metabolite, or a pharmaceutically acceptable salt, solvate, hydrate, or clathrate thereof. Preferably, the bupropion metabolite is an optically pure bupropion metabolite. Preferred optically active bupropion metabolites are (S,S)-hydroxybupropion, (S,S)-dihydrobupropion, (R,R)-dihydrobupropion, (R,S)-dihydrobupropion, and (S,R)-dihydrobupropion. A specific preferred optically pure bupropion metabolite is (S,S)-hydroxybupropion. In a preferred method encompassed by this embodiment, adverse effects associated with the inhibition of dopamine reuptake are reduced or avoided. In another method encompassed by this embodiment, the bupropion metabolite or pharmaceutically acceptable salt, solvate, hydrate, or clathrate thereof is adjunctively administered with an additional pharmacologically active compound, i.e., the bupropion metabolite and additional pharmacologically active compound are administered as a combination, concurrently but separately, or sequentially by any suitable route (e.g., orally, transdermally, or mucosally).

Additional pharmacologically active compounds include, but are not limited to, SSRIs, 5-HT$_3$ inhibitors, and nicotine.

SSRIs are compounds that inhibit the central nervous system uptake of serotonin while having reduced or limited affinity for other neurologically active receptors. Examples of SSRIs include, but are not limited to, citalopram (CELEXA®, Parke-Davis); fluoxetine (PROZAC®, Eli Lilly & Co.) fluvoxamine (LUVOX®, Solvay Pharmaceuticals, Inc.); paroxetine (PAXIL®, SmithKline Beecham Pharmaceuticals); sertraline (ZOLOFT®, Pfizer); venlafaxine (EFFEXOR®, Wyeth-Ayerst Laboratories); and optically pure stereoisomers, active metabolites, and pharmaceutically acceptable salts, solvates, hydrates, and clathrates thereof. Preferred 5-HT$_3$ antagonists are antiemetic agents. Examples of suitable 5-HT$_3$ antagonists include, but are not limited to, granisetron (KYTRIL®, SmithKline Beecham Pharmaceuticals), metoclopramide (REGLAN®, A. H. Robins), ondansetron (ZOFRAN®, Glaxo Wellcome Inc.), norcisapride, renzapride, zacopride, tropisetron, and optically pure stereoisomers, active metabolites, and pharmaceutically acceptable salts, solvates, hydrates, and clathrates thereof.

A second embodiment of the invention encompasses a method of treating or preventing sexual dysfunction which comprises administering to a patient in need of such treatment or prevention a therapeutically or prophylactically effective amount of a bupropion metabolite or a pharmaceutically acceptable salt, solvate, hydrates, or clathrate thereof. Preferably, the bupropion metabolite is an optically pure bupropion metabolite. Preferred optically pure bupropion metabolites are (S,S)-hydroxybupropion, (S,S)-dihydrobupropion, (R,R)-dihydrobupropion, (R,S)-dihydrobupropion, and (S,R)-dihydrobupropion. A specific preferred optically pure bupropion metabolite is (S,S)-hydroxybupropion. In one method encompassed by this embodiment, the bupropion metabolite or pharmaceutically acceptable salt, solvate, hydrate or clathrate thereof is administered transdermally or mucosally (e.g., nasally, sublingually, or buccally). In another method encompassed by this embodiment, the bupropion metabolite or pharmaceutically acceptable salt, solvate, hydrate or clathrate thereof is adjunctively administered with a 5-HT$_3$ antagonist. Another method encompassed by this embodiment is a method of treating or preventing erectile dysfunction.

A third embodiment of the invention encompasses a method of treating or preventing an affective disorder which comprises administering to a patient in need of such treatment or prevention a therapeutically or prophylactically effective amount of a bupropion metabolite, or a pharmaceutically acceptable salt, solvate, hydrate, or clathrate thereof. This embodiment encompasses the treatment or prevention of affective disorders such as, but not limited to, depression, anxiety disorders, attention deficit disorder, attention deficit disorder with hyperactivity, attention deficit hyperactivity disorder, bipolar and manic conditions, sexual dysfunction, psycho-sexual dysfunction, bolimia, obesity or weight gain, nareolepsy, chronic fatigue syndrome, seasonal affective disorder, premenstrual syndrome, and substance addiction or abuse. Preferably, the bupropion metabolite is an optically pure bupropion metabolite. Preferred optically pure bupropion metabolites are (S,S)-hydroxybupropion, (S,S)-dihydrobupropion, (R,R)-dihydrobupropion, (R,S)-dihydrobupropion, and (S,R)-dihydrobupropion. A specifically preferred optically pure bupropion metabolite is (S,S)-hydroxybupropion. One method encompassed by this embodiment is a method of treating, or preventing depression. Another method encompassed by this embodiment is a method of treating or preventing nareolepsy. Yet another method encompassed by this embodiment is a method of treating or preventing nicotine addiction.

A fourth embodiment of the invention encompasses a method of treating or preventing a cerebral function disorder which comprises administering to a patient in need of such treatment or prevention a therapeutically or prophylactically effective amount of a bupropion metabolite, or a pharmaceutically acceptable salt, solvate, hydrate, or clathrate thereof. This embodiment encompasses the treatment or prevention of cerebral function disorders such as, but not limited to, senile dementia, Alzheimer's type dementia, memory loss, amnesia/amnestic syndrome, epilepsy, disturbances of consciousness, coma, lowering of attention, speech disorders, Parkinson's disease, Lennox syndrome, autistic disorder, autism, hyperkinetic syndrome, schizophrenia, cerebral infaretion, cerebral bleeding, cerebral autcriosclerosis, cerebral venous thrombosis, and head injury. Preferably, the bupropion metabolite is an optically pure bupropion metabolite. Preferred optically pure bupropion metabolites are (S,S)-hydroxybupropion, (S,S)-dihydrobupropion, (R,R)-dihydrobupropion, (R,S)-dihydrobupropion, and (S,R)-dihydrobupropion. A specifically preferred optically pure bupropion metabolite is (S,S)-hydroxybupropion. A particular method encompassed by this embodiment is a method of treating or preventing Parkinson's disease. Another method encompassed by this embodiment is a method of treating or preventing epilepsy.

A fifth embodiment of the invention encompasses a method of eliciting smoking cessation which comprises administering to a patient who smokes tobacco a therapeutically effective amount of a bupropion metabolite, or a pharmaceutically acceptable salt, solvate, hydrate, or clathrate thereof. Preferably, the bupropion metabolite is an optically pure bupropion metabolite. Preferred optically pure bupropion metabolites are (S,S)-hydroxybupropion, (S,S)-dihydrobupropion, (R,R)-dihydrobupropion, (R,S)-dihydrobupropion, and (S,R)-dihydrobupropion. A specifically preferred optically pure bupropion metabolite is (S,S)-hydroxybupropion. In one method encompassed by this embodiment, the bupropion metabolite or pharmaceutically acceptable salt, solvate, hydrate, or clathrate thereof is administered orally, mucosally, or transdermally. In a preferred method, the bupropion metabolite, or pharmaceutically acceptable salt, solvate, hydrate, or clathrate thereof, is administered transdermally. In another method encompassed by this embodiment, the bupropion metabolite or pharmaceutically acceptable salt, solvate, hydrate, or clathrate thereof is adjunctively administered with an amount of nicotine or a muscarinic receptor antagonist, such as, but not limited to, ipratropium bromide. Preferably, the nicotine and/or bupropion metabolite, or pharmaceutically acceptable salt, solvate, hydrate, or clathrate thereof, is administered orally, mucosally, or transdermally. More preferably, the nicotine and/or bupropion metabolite, or pharmaceutically acceptable salt, solvate, hydrate, or clathrate thereof is administered transdermally.

A sixth embodiment of the invention encompasses a method of treating or preventing incontinence which comprises administering to a patient in need of such treatment or prevention a therapeutically or prophylactically effective amount of a bupropion metabolite, or a pharmaceutically acceptable salt, solvate, hydrate, or clathrate thereof. Preferably, the bupropion metabolite is an optically pure bupropion metabolite. Preferred optically pure bupropion metabolites are (S,S)-hydroxybupropion, (S,S)-dihydrobupropion, (R,R)-dihydrobupropion, (R,S)-dihydrobupropion, and (S,R)-dihydrobupropion. A specifically preferred optically pure bupropion metabolite is (S,S)-hydroxybupropion. One method encompassed by this embodiment is a method of treating or preventing stress urinary incontinence. In another method encompassed by this embodiment, the patient is a human of an age greater than 50 years or less than 13 years.

A seventh embodiment of the invention encompasses pharmaceutical compositions and dosage forms which comprise a bupropion metabolite, or a pharmaceutically acceptable salt, solvate, hydrate, or clathrate thereof. Preferably, the bupropion metabolite is an optically pure bupropion metabolite. Preferred optically pure bupropion metabolites are (S,S)-hydroxybupropion, (S,S)-dihydrobupropion, (R,R)-dihydrobupropion, (R,S)-dihydrobupropion, and (S,R)-dihydrobupropion. A specifically preferred optically pure bupropion metabolite is optically pure (S,S)-hydroxybupropion. Pharmaceutical compositions and dosage forms encompassed by this embodiment can further comprise at least one additional pharmacologically active compound. Additional pharmacologically active compounds include, but are not limited to, SSRIs, 5-HT$_3$ inhibitors, and nicotine as described above.

An eighth embodiment of the invention encompasses a process for preparing optically pure (S,S)-hydroxybupropion which comprises: asymmetric dihydroxylation of Z-1-(3-chlorophenyl)-1-tert-butyldimethylsilyloxy-1-propene to form an intermediate; contacting the intermediate with 2-amino-2-methyl-1-propanol under reaction conditions suitable for the formation of (S,S)-2-(3-chlorophenyl)-2-hydroxy-3,5,5-trimethyl-morpholinol; and isolating the (S,S)-2-(3-chlorophenyl)-2-hydroxy-3,5,5-trimethyl-morpholinol. Preferably, the intermediate formed by the asymmetric dihydroxylation is an α-hydroxy ketone activated by trifluoromethane sulfonic anhydride. Various solvent systems can be used for the preceding steps including, but not limited to, acetonitrile, acetone, alcohols, esters, ethers, water, and combinations thereof.

A ninth embodiment of the invention encompasses a process for preparing optically pure (R,R)-hydroxybupropion which comprises: the asymmetric dihydroxylation of Z-1-(3-chlorophenyl)-1-tert-butyldimethylsilyloxy-1-propene to form an intermediate; the reaction of the intermediate with 2-amino-2-methyl-1-propanol to form (R,R)-2-(3-chlorophenyl)-2-hydroxy-3,5,5-trimethyl-morpholinol; and the isolation of the (R,R)-2-(3-chlorophenyl)-2-hydroxy-3,5,5-trimethyl-morpholinol. Preferably, the intermediate formed by the asymmetric dihydroxylation is an α-hydroxy ketone activated by trifluoromethane sulfonic anhydride. Various solvent systems can be used for the preceding steps including, but not limited to, acetonitrile, acetone, alcohols, esters, ethers, water, and combinations thereof.

A tenth embodiment encompasses a process for preparing optically pure 2-(3-chlorophenyl)-2-hydroxy-3,5,5-trimethyl-morpholinol or a pharmaceutically acceptable salt, solvate, hydrate, or clathrate thereof which comprises: brominating 2-chloropropiophenone to form an intermediate; reacting the intermediate with 2-amino-2-methyl-1-propanol to form racemic 2-(3-chlorophenyl)-2-hydroxy-3,5,5-trimethyl-morpholinol; resolving the racemic 2-(3-chlorophenyl)-2-hydroxy-3,5,5-trimethyl-morpholinol; and isolating the optically pure 2-(3-chlorophenyl)-2-hydroxy-3,5,5-trimethyl-morpholinol. Various resolution techniques for the separation of the racemates can be used, including but not limited to chiral chromatography, enzymatic resolution, conversion to diastereomers. In a particular embodiment, the resolution can encompass contacting the racemates with an acid to form diastereomeric salts. In a preferred process encompassed by this embodiment, the formation of diastercomeric salts and separation of the diastereomeric salts gives a mother liquor that is treated with a second chiral acid to form second diastereomeric salts, which are then separated, and treated with base to give an optically pure enantiomer. Various solvent systems can be used for the preceding steps including, but not limited to, acetonitrile, acetone, alcohols, esters, ethers, water, and combinations thereof.

An eleventh embodiment encompasses a process for preparing racemic erythro-dihydrobupropion or a pharmaceutically acceptable salt, solvate, hydrate, or clathrate thereof, which comprises reducing racemic bupropion with a suitable reducing agent to form a racemic eiythro/threo mixture and purifying the racemic erythro-dihydrobupropion. Preferred techniques for purification, include but are not limited to, crystallization, filtration, and chromatography. Various solvent systems can be used for the preceding steps including, but not limited to, acetonitrile, ketones, alcohols, esters, ethers, water, and combinations thereof.

A twelfth embodiment encompasses a process for preparing optically pure erythro dihydrobupropion or a pharmaceutically acceptable salt, solvate, hydrate, or clathrate thereof, which comprises: contacting 3-chloropropiophenlone with a silyl halide under reaction conditions suitable for the fomnation of Z-1-(3-chlorophenyl)-1-silyloxy-1-propene, asymmetric dihydroxylation of Z-1-(3-chlorophenyl)-1-silyloxy-1-propene to yield 3-chloro-2-(R)-hydroxyl-propiophenone; reaction of 3-chloro-2-(R)-hydroxyl-propiophenone under suitable conditions with tert-butylamine, and reduction and purification of the resulting product to afford optically pure erythro dihydrobupropion. In a particular embodiment, the erythro dihydrobupropion is stirred in an acid and then crystallized to give optically pure erythro dihydrobupropion acid salt. In a preferred embodiment, the 3-chloropropiophenone and the silyl halide are reacted in the presence of a base, including but not limited to, lithium diisopropylamide (LDA) and lithium hexamethyl disilylamide (LiHMDS). In another preferred embodiment, the silyl halide is selected from the group containing, but not limited to, trimethyl silyl chloride (TMSCl), tributyl silyl chloride, and tert-butyldimethylsilyl chloride. The silyl halide is preferably tert-butyldimethylsilyl chloride. In another preferred embodiment, the hydroxy group of 3-chloro-2-(R)-hydroxyl-propiophenone is converted to a leaving group, preferably a tosylate, mesylate, or nosylate and more preferably a triflate. In another embodiment, the reduction of the ketone is achieved preferably using a metal hydride, more preferably Red-A1. Techniques for purification include, but are not limited to, filtration, crystallization, and chromatography. Various solvent systems can be used for the preceding steps including, but not limited to, acetonitrile, ketones, alcohols, esters, ethers, water, and combinations thereof.

4.1 Synthesis of Bupropion Metabolites

The metabolism of bupropion, which varies among species, is complex and poorly understood. Bupropion has been shown to induce its own metabolism in mice, rats, and dogs, and may do so in human patients to whom the drug has been administered over long periods of time. In the plasma of healthy humans to whom the drug has been administered, however, at least three major metabolites are found. See, e.g., *Physicians' Desk Reference®* 1252–1258 (53$^{rd}$ ed. 1999). Each of these major metabolites is chiral, meaning that a total of at least ten optically pure bupropion metabolites exist in varying concentrations in the plasma of a patient following administration of the drug.

It is possible to prepare enantiomers of bupropion and racemic threo dihydrobupropion using techniques known to those skilled in the art. See, e.g., Musso et al. *Chirality*, 5:495–500 (1993). It is also possible to prepare a mixture of the stereoisomers of the amino alcohol metabolite of bupropion (i.e., 1-(3-chlorophenyl)-2-[(1,1-dimethylethanol) amino]-1-propanol) using techniques known to those skilled in the art. See, e.g., Japanese Patent No. 63091352. The optically pure forms of this metabolite can be isolated from the resulting mixture by any method known to those skilled in the art, including high performance liquid chromatography (HPLC) and the formation and crystallization of chiral salts. See, e.g., Jacques, J., et al., *Enantiomers, Racemates and Resolutions* (Wiley-Interscience, New York, 1981); Wilen, S. H., et al., *Tetrahedron*, 33:2725 (1977); Eliel, E. L., *Stereochemistry of Carbon Compounds* (McGraw-Hill, N.Y., 1962); and Wilen, S. H., *Tables of Resolving Agents and Optical Resolving* p. 268 (E. L. Eliel, Ed., Univ. of Notre Dame Press, Notre Dame, Ind., 1972). However, prior to the present invention these methods resulted in low yields and low enantiomeric excess. In addition, resolution was very expensive and not suitable for large scale production.

When a mixture of enantiomeric bases interacts with an optically active acid, diastereomeric salts are formed. These diastereomeric salts have different physical properties and can advantageously be separated by methods based on these differences, which methods include but are not limited to, distillation, chromatographic separation, and fractional crystallization. One method encompassed by this invention utilizes a chiral acid to resolve racemic hydroxybupropion to give its diastereomeric salts. Suitable chiral acids include, but are not limited to, optically pure derivatives of camphor, α-hydroxy acetic acid, tartaric acid, malic acid, and mandelic acid. Moreover, those skilled in the art would recognize that resolution can be achieved by reacting any chiral acid with a racemic base to form a diasteromeric salt. See e.g., Juaristi, E., *Introduction to Stereochemistry & Confomational Analysis* pp. 144–151 (John Wiley and Sons, Inc., New York, 1991); Eliel, E. L., *Stereochemistry of Carbon Compounds* pp. 49–53 (McGraw-Hill, N.Y., 1962); Fitzi, R. and Seebach, D., *Angew. Chem. Int. Ed.*, 25:345 (1986); Gharpure, M. M. and Rao, A. S., *Synthesis* 410 (1988).

For example, (R,R)-hydroxybupropion free base can be isolated by reacting the diastereomerically pure salt with a base such as sodium hydroxide, potassium carbonate, potassium hydroxide, and ammonium hydroxide to obtain the optically pure enantiomer. The ratio of the resolving acid to racemic hydroxybupropion is from about 0.01:1 to about 5:1. In a particular embodiment, the racemic hydroxybupropion present in the mother liquor of a crystallization separation step can be treated with a second chiral acid to give a diasteromeric salt which can be resolved and reacted with a base to afford optically pure (S,S)-hydroxybupropion as outlined in Scheme 4:

Scheme 4

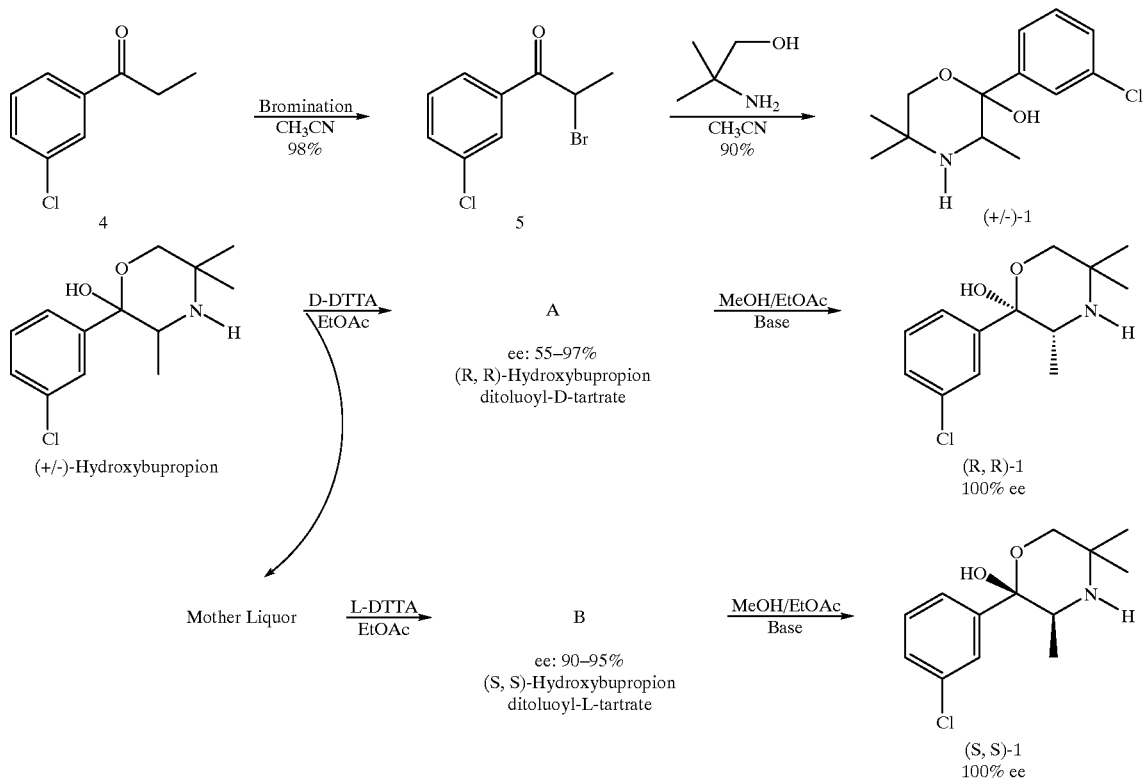

In the embodiment represented by Scheme 4, racemic hydroxybupropion can be resolved with a chiral acid such as L-DTTA, and the mother liquor can subsequently be treated with D-DTTA to afford (S,S)-hydroxybupropion and (R,R)-hydroxybupropion, respectively. Various solvent systems can be used for the chiral acid resolving steps including, but not limited to, acetonitrile, ketones, alcohols, esters, ethers, water, and combinations thereof.

It is also possible to prepare a mixture of the stereoisomers of the tert-butyl alcohol metabolite of bupropion (i.e., 1-(3-chlorophenyl)-2-[(1,1-dimethylethanol)amino]-1-propanone). From the resulting mixture of compounds, individual stereoisomers can be resolved using conventional means such as high performance liquid chromatography (HPLC) and the formation and crystallization of chiral salts.

In the embodiment represented by Scheme 5 below, an effective, efficient, and novel process utilizes a protected alcohol derivative of 1-(3-chlorophenyl)-1-propene, which is dihydroxylated and then cyclized to form the morpholinol moiety. A particular embodiment of this process which can be used to form optically pure (R,R)- and (S,S)-hydroxybupropion is shown in Scheme 5:

Scheme 5

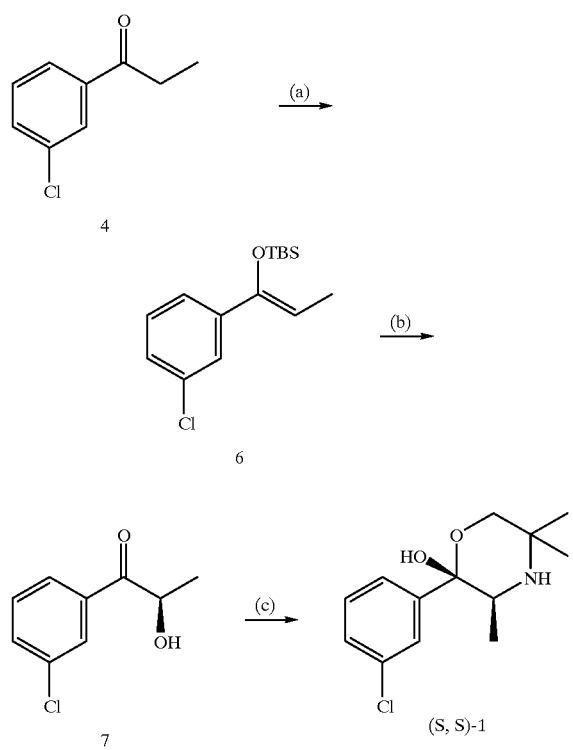

According to a preferred embodiment of this process, compound 6 is prepared in step (a), wherein the ketone 4 is converted to its enolate, preferably by use of a strong base such as, but not limited to, lithium hexamethyldisilazide (LiHMDS) and lithium diisopropylamide (LDA). A preferred base is LDA. The enolate is then trapped using a protecting agent such as, but not limited to, tert-butyldimethylsilyl chloride (TBSCl). Compound 6 is preferably isolated prior to step (b).

According to step (b), the vinyl group of compound 6 is asymmetrically dihydroxylated to give the ketone. It has been found that the choice of reagent used to asymmetrically hydroxylate compound 6 affects the stereochemistry of the resulting product, as well as its optical purity (enantiomeric excess). Suitable asymmetric hydroxylation reagents include, for example, oxides of transition metals such as manganese and osmium, although preferred reagents are AD-mix-α and AD-mix-β. These reagents have been found to selectively dihydroxylate the vinyl group of compound 6 to reform the ketone. Use of AD-mix-β yields (R)-3-chloro-2-hydroxyl-propiophenone, while use of AD-mix-α yields (S)-3-chloro-2-hydroxyl-propiophenone. Although not necessary, it has been found that care taken to ensure the optical purity of the intermediate (e.g., compound 7) formed in this step improves the optical purity of the final product (i.e., optically pure hydroxybupropion). It is thus preferred that step (b) further include purification by, for example, column chromatography.

Substantially optically pure (S,S)-hydroxybupropion 1 is formed in step (c) of Scheme 5, which comprises the stereospecific displacement of triflates of compound 7:

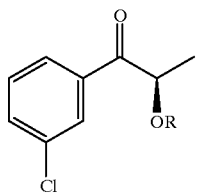

wherein R is triflate (i.e., —OSO$_2$CF$_3$). Other compounds potentially useful in the synthesis of compounds of the invention are those wherein R is mesylate, tosylate, or nosylate. Substantially optically pure (R,R)-hydroxybupropion is preferably formed from the triflate of opposite stereochemistry.

Triflation is preferably conducted with pyridine base. A preferred base is lutidine when used in combination with trifluoromethanesulfonic anhydride. The cyclized product 1 is isolated by extraction, and purified by chromatography. Substantially optically pure (R,R)-hydroxybupropion is formed in the same way if step (b) yields (S)-3-chloro-2-hydroxyl-propiophenone.

The present invention further encompasses an efficient synthetic process for the synthesis of racemic erythro-dihydrobupropion as shown in Scheme 6:

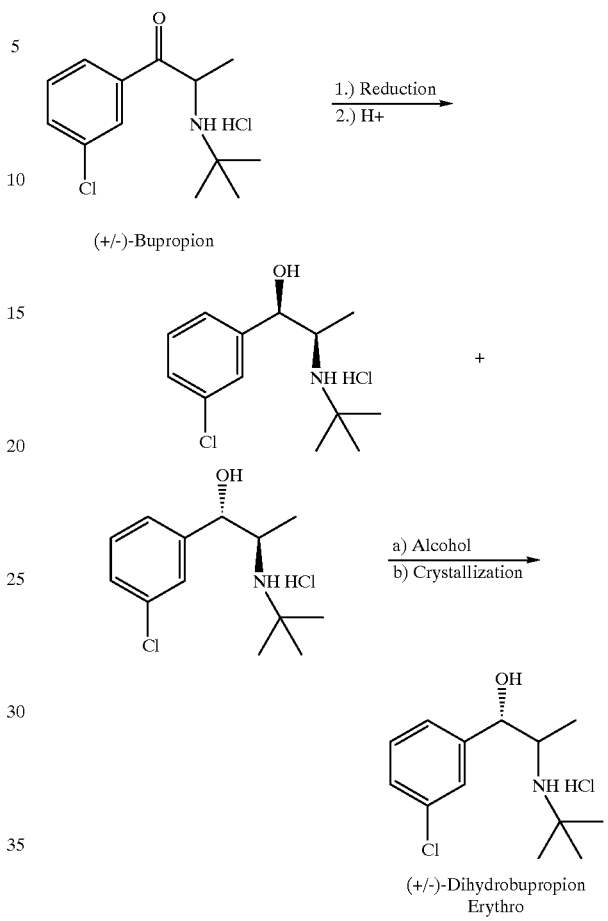

According to this method, erythro dihydrobupropion is synthesized by reducing racemic bupropion in a non-polar solvent such as, but not limited to, benzene, toluene, xylene, and mixtures thereof. A preferred reducing agent is a metal hydride, more preferably Red-Al. In a particular embodiment, the erythro-dihydrobupropion is treated with an acid, preferably hydrochloric acid, and then crystallized by refluxing in alcohol. In a preferred embodiment, the alcohol is methanol, ethanol, propanol, butanol, isopropanol, or a mixture thereof. A preferred alcohol is isopropanol.

The present invention also embodies a method of preparing optically pure erythro-dihydrobupropion. An example of this method is shown in Scheme 7:

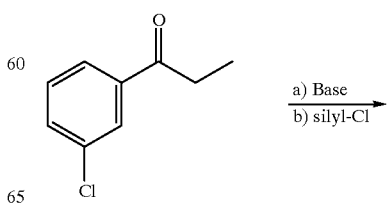

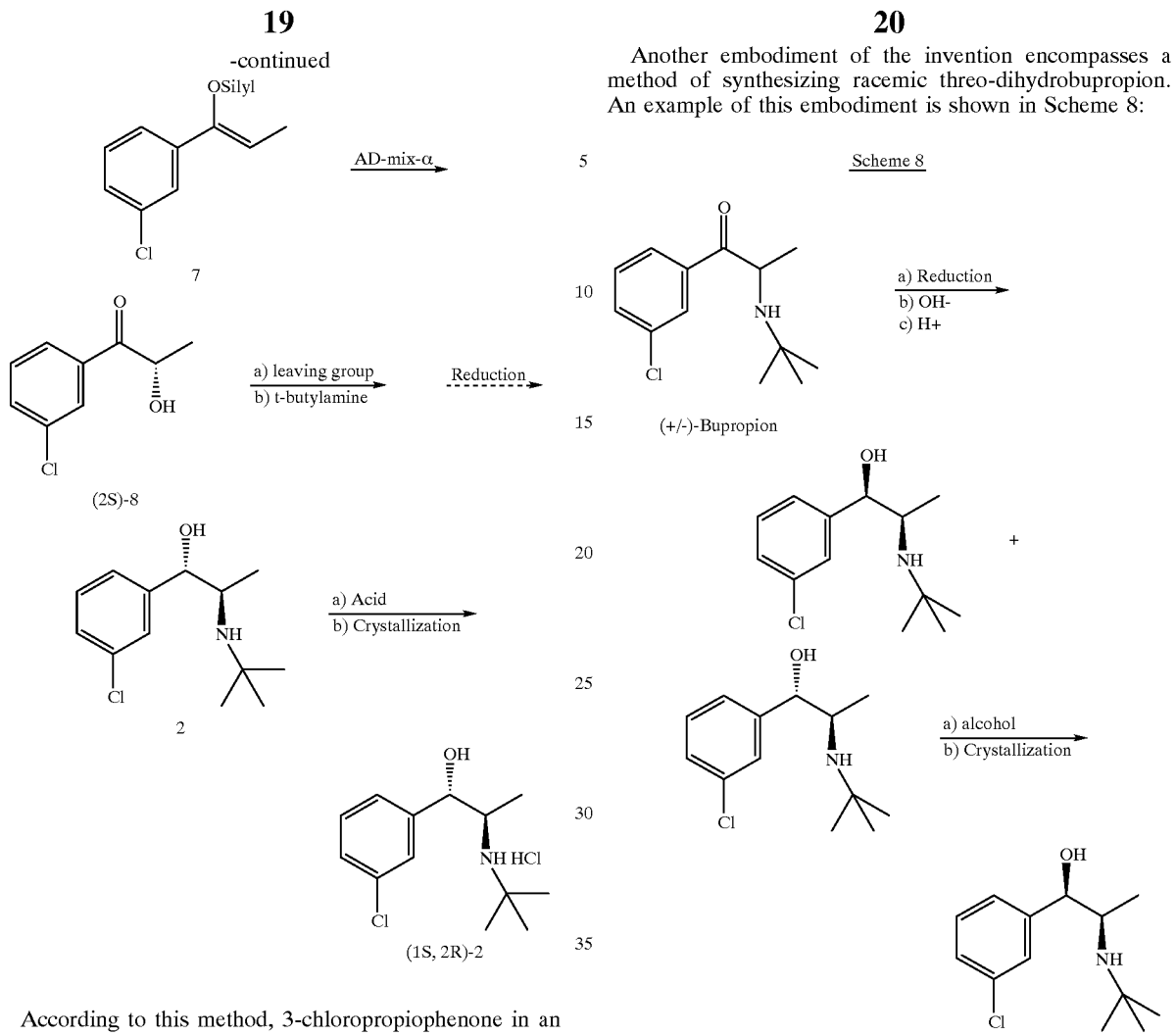

According to this method, 3-chloropropiophenone in an ether solvent is contacted with a base, preferably LDA or LiHMDS, optionally in the presence of chelating agent such as hexamethylphosphoramide (HMPA). Examples of ether solvents include, but are not limited to, tetrahydrofuran. The mixture is stirred at low temperature, preferably about −78° C. A silyl halide such as tert-butyl dimethylsilyl chloride is then added to trap the enolate. The vinyl group of compound is then asymmetrically dihydroxylated to give the ketone. It has been found that the choice of reagent used to asymmetrically hydroxylate compound affects the stereochemistry of the resulting product, as well as its optical purity (enantiomeric excess). Suitable asymmetric hydroxylation reagents include, for example, oxides of transition metals such as manganese and osmium, although preferred reagents are AD-mix-α and AD-mix-β.

For example, a silyl enolate can be asymmetrically hydroxylated using AD-mix α and methanesulfonamide to give 3'-chloro-2-(R)-hydroxyl-propiophenone. The hydroxyl group is then converted to a leaving group and tert-butylamine is added, followed by reduction, preferably with a metal hydride reducing agent, more preferably with Red-Al to give the erythro-(R,S)-dihydrobupropion. In a particular embodiment, this is then dissolved in an ether, preferably methyl tert-butyl ether, and stirred in acid, preferably hydrochloric acid, and subsequently refluxed in an alcohol, preferably isopropanol.

In an alternative to the embodiment shown in Scheme 7, AD-mix α can used to obtain erythro-(S,R)-dihydrobupropion.

Another embodiment of the invention encompasses a method of synthesizing racemic threo-dihydrobupropion. An example of this embodiment is shown in Scheme 8:

According to this method, racemic bupropion hydrochloride is reduced with a reducing agent, such as, but not limited to, THF-borane to give an erythro/threo mixture of dihydrobupropion hydrochloride. This mixture is then purified by, for example, treating it with an acid, preferably hydrochloric acid. Refluxing in an alcohol, such as but not limited to, isopropanol, followed by crystallization yields the pure racemic threo-dihydrobupropion.

4.2 Biological Activities of Bupropion Metabolites

Bupropion metabolites can be screened for their ability to inhibit the reuptake of the neuronal monoamines norepinephrine (NE), dopamine (DA), and serotonin (5-HT). Norepinephrine reuptake inhibition can be determined using the general procedure described by Moisset, B., et al., *Brain Res.*, 92:157–164 (1975); dopamine reuptake inhibition can be determined using the general procedures described by Janowsky, A., et al., *J. Neurochem.* 46:1272–1276 (1986); and serotonin reuptake inhibition can be determined using the general procedures described by Perovic, S. and Muller, W. E. G., *Brain Res.* 92:157–164 (1995). Other assays known to those skilled in the art may also be used.

4.3. Pharmaceutical Compositions and Method of Use

The magnitude of a prophylactic or therapeutic dose of an active ingredient in the acute or chronic management of a disorder or condition will vary with the severity of the disorder or condition to be treated and the route of administration. The dose, and perhaps the dose frequency, will also vary according to age, body weight, response, and the past medical history of the patient. Suitable dosing regimens can be readily selected by those skilled in the art with due consideration of such factors.

Suitable daily doses for the treatment or prevention of a disorder described herein can be readily determined by those skilled in the art. A recommended dose of racemic or optically pure bupropion metabolite is from about 1 mg to about 750 mg per day, given as a single once-a-day dose in the morning or as a single or divided doses throughout the day. Preferably, a daily dose is from about 5 mg to about 700 mg per day, more preferably from about 10 mg to about 650 mg per day.

Suitable daily dosage ranges of second pharmacologically active compounds that can be adjunctively administered with a racemic or optically pure bupropion metabolite can be readily determined by those skilled in the art following dosages reported in the literature and recommended in the Physicians's Desk Reference® (53$^{rd}$ ed., 1999).

For example, suitable daily dosage ranges of 5-HT$_3$ antagonists can be readily determined by those skilled in the art and will vary depending on factors such as those described above and the particular 5-HT$_3$ antagonists used. In general, the total daily dose of a 5-HT$_3$ antagonist for the treatment or prevention of a disorder described herein is from about 0.5 mg to about 500 mg, preferably from about 1 mg to about 350 mg, and more preferably from about 2 mg to about 250 mg per day.

Suitable daily dosage ranges of nicotine can also be readily determined by those skilled in the art and will vary depending on factors such as those described above. In general, the total daily dose of nicotine for the treatment or prevention of a disorder described herein is from about 1 mg to about 60 mg, preferably from about 8 mg to about 40 mg, and more preferably from about 10 mg to about 25 mg per day.

The therapeutic or prophylactic administration of an active ingredient of the invention is preferably initiated at a lower dose, e.g., from about 1 mg to about 75 mg of bupropion metabolite and optionally from about 15 mg to about 60 mg of 5-HT$_3$ antagonist, and increased, if necessary, up to the recommended daily dose as either a single dose or as divided doses, depending on the global response of the patient. It is further recommended that patients aged over 65 years should receive doses of bupropion metabolite in the range of from about 1 mg to about 375 mg per day depending on global response. It may be necessary to use dosages outside these ranges, which will be readily determinable by one of ordinary skill in the pharmaceutical art.

The dosage amounts and frequencies provided above are encompassed by the terms "therapeutically effective," "prophylactically effective," and "therapeutically or prophylactically effective" as used herein. When used in connection with an amount of a racemic or optically pure bupropion metabolite, these terms further encompass an amount of racemic or optically pure bupropion metabolite that induces fewer or less severe adverse effects than are associated with the administration of racemic bupropion.

Any suitable route of administration can be employed for providing the patient with a therapeutically or prophylactically effective dose of an active ingredient. For example, oral, mucosal (e.g., nasal, sublingual, buccal, rectal, vaginal), parenteral (e.g., intravenous, intramuscular), transdermal, and subcutaneous routes can be employed. Preferred routes of administration include oral, transdermal, and mucosal. As mentioned above, administration of an active ingredient for the treatment or prevention of erectile dysfunction is preferably mucosal or transdermal. Suitable dosage forms for such routes include, but are not limited to, transdermal patches, ophthalmic solutions, sprays, and aerosols. Transdermal compositions can also take the form of creams, lotions, and/or emulsions, which can be included in an appropriate adhesive for application to the skin or can be included in a transdennal patch of the matrix or reservoir type as are conventional in the art for this purpose.

A preferred transdermal dosage form is a "reservoir type" or "matrix type" patch, which is applied to the skin and worn for a specific period of time to permit the penetration of a desired amount of active ingredient. Examples of transdermal dosage forms and methods of administration that can be used to administer the active ingredient(s) of the invention include, but are not limited to, those disclosed in U.S. Pat. Nos.: 4,624,665; 4,655,767; 4,687,481; 4,797,284; 4,810,499; 4,834,978; 4,877,618; 4,880,633; 4,917,895; 4,927,687; 4,956,171; 5,035,894; 5,091,186; 5,163,899; 5,232,702; 5,234,690; 5,273,755; 5,273,756; 5,308,625; 5,356,632; 5,358,715; 5,372,579; 5,421,816; 5,466,465; 5,494,680; 5,505,958; 5,554,381; 5,560,922; 5,585,111; 5,656,285; 5,667,798; 5,698,217; 5,741,511; 5,747,783; 5,770,219; 5,814,599; 5,817,332; 5,833,647; 5,879,322; and 5,906,830, the disclosures of which are incorporated herein by reference.

An example of a transdermal dosage form of the invention comprises a bupropion metabolite and/or a second pharmacologically active compound in a patch form. The patch is won for 24 hours and provides a total daily dose of from about 1 mg to about 750 mg per day. Preferably, a daily dose is from about 5 mg to about 700 mg per day, more preferably, from about 10 mg to about 650 mg per day. The patch can be replaced with a fresh patch when necessary to provide constant administration of the active ingredient to the patient.

Other dosage forms of the invention include, but are not limited to, tablets, coated tablets, caplets, troches, lozenges, dispersions, suspensions, suppositories, ointments, cataplasms (poultices), pastes, powders, dressings, creams, plasters, solutions, capsules, soft elastic gelatin capsules, sustained release formulations, and patches.

In one embodiment, pharmaceutical compositions and dosage forms of the invention comprise a racemic or optically pure bupropion metabolite, or a pharmaceutically acceptable salt, solvate, hydrate, or clathrate thereof, and optionally a second pharmacologically active compound, such as a SSRI, a 5-HT$_3$ antagonist, or nictotine. Preferred optically pure bupropion metabolites are (R,R)-2-(3-chlorpheniyl)-2-hydroxy-3,5,5-trimethyl-morpholinol; (S,S)-2-(3-chlorophenyl)-2-hydroxy-3,5,5-trimethyl-morpholinol; (R,R)-1-(3-chlorophenyl)-2-[(1,1-dimethylethanol)amino]-1-propanol; (S,R)-1-(3-chlorophenyl)-2-[(1,1-dimethylethanol)amino]-1-propanol; (S,S)-1-(3-chlorophenyl)-2-[(1,1-dimethylethanol)amino]-1-propanol; and (R,S)-1-(3-chlorophenyl)-2-[(1,1-dimethylethanol)amino]-1-propanol. The pharmaceutical compositions and dosage forms can contain a pharmaceutically acceptable carrier and optionally other therapeutic ingredients known to those skilled in the art.

In practical use, an active ingredient can be combined in an intimate admixture with a pharmaceutical carrier according to conventional pharmaceutical compounding techniques. The carrier can take a wide variety of forms depending on the form of preparation desired for administration. In preparing the compositions for an oral dosage form, any of the usual pharmaceutical media can be employed as carriers, such as, for example, water, glycols, oils, alcohols, flavoring agents, preservatives, coloring agents, and the like in the case of oral liquid preparations (such as suspensions, solutions, and elixirs) or aerosols; or carriers such as starches, sugars, micro-crystalline cellulose, diluents, granulating agents, lubricants, binders, and disintegrating agents can be used in the case of oral solid preparations, preferably without employing the use of lactose. For example, suitable carriers include powders, capsules, and tablets, with the solid oral preparations being preferred over the liquid preparations.

Because of their ease of administration, tablets and capsules represent the most advantageous oral dosage unit forms, in which case solid pharmaceutical carriers are employed. If desired, tablets can be coated by standard aqueous or nonaqueous techniques.

In addition to the common dosage forms set out above, an active ingredient can also be administered by controlled release means or delivery devices that are well known to those of ordinary skill in the art, such as those described in U.S. Pat. Nos.: 3,845,770; 3,916,899; 3,536,809; 3,598,123; 4,008,719; 5,674,533; 5,059,595; 5,591,767; 5,120,548; 5,073,543; 5,639,476; 5,354,556; and 5,733,566, the disclosures of which are incorporated herein by reference. These dosage forms can be used to provide slow or controlled-release of one or more active ingredients using, for example, hydroxypropylmethyl cellulose, other polymer matrices, gels, permeable membranes, osmotic systems, multilayer coatings, microparticles, liposomes, or microspheres or a combination thereof to provide the desired release profile in varying proportions. Suitable controlled-release formulations known to those of ordinary skill in the art, including those described herein, can be readily selected for use with the pharmaceutical compositions of the invention. The invention thus encompasses single unit dosage forms suitable for oral administration such as, but not limited to, tablets, capsules, gelcaps, and caplets that are adapted for controlled-release.

All controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include: 1) extended activity of the drug; 2) reduced dosage frequency; and 3) increased patient compliance. In addition, controlled-release formulations can be used to affect the time of onset of action or other characteristics, such as blood levels of the drug, and thus can affect the occurrence of side effects.

Most controlled-release formulations are designed to initially release an amount of drug that promptly produces the desired therapeutic effect, and gradually and continually release of other amounts of drug to maintain this level of therapeutic effect over an extended period of time. In order to maintain this constant level of drug in the body, the drug must be released from the dosage form at a rate that will replace the amount of drug being metabolized and excreted from the body. Controlled-release of an active ingredient can be stimulated by various inducers, including, but not limited to, pH, temperature, enzymes, water, or other physiological conditions or compounds.

Pharmaceutical compositions of the invention suitable for oral administration can be presented as discrete dosage forms, such as capsules, cachets, or tablets, or aerosol sprays each containing a predetermined amount of an active ingredient as a powder or in granules, a solution, or a suspension in an aqueous or non-aqueous liquid, an oil-in-water emulsion, or a water-in-oil liquid emulsion. Such dosage forms can be prepared by any of the methods of pharmacy, but all methods include the step of bringing the active ingredient into association with the carrier, which constitutes one or more necessary ingredients. In general, the compositions are prepared by uniformly and intimately admixing the active ingredient with liquid carriers or finely divided solid carriers or both, and then, if necessary, shaping the product into the desired presentation.

For example, a tablet can be prepared by compression or molding, optionally with one or more accessory ingredients. Compressed tablets can be prepared by compressing in a suitable machine the active ingredient in a free-flowing form such as powder or granules, optionally mixed with an excipient such as, but not limited to, a binder, a lubricant, an inert diluent, and/or a surface active or dispersing agent. Molded tablets can be made by molding in a suitable machine a mixture of the powdered compound moistened with an inert liquid diluent.

This invention further encompasses lactose-free pharmaceutical compositions and dosage forms. Because the major human metabolites of bupropion are secondary amines, they can potentially decompose over time when exposed to lactose. Compositions of the invention that comprise bupropion metabolites preferably contain little, if any, lactose other mono- or di-saccharides. As used herein, the term "lactose-free" means that the amount of lactose present, if any, is insufficient to substantially increase the degradation rate of an active ingredient.

Lactose-free compositions of the invention can comprise excipients which are well known in the art and are listed in the USP (XXI)/NF (XVI), which is incorporated herein by reference. In general, lactose-free compositions comprise an active ingredient, a binder/filler, and a lubricant in pharmaceutically compatible and pharmaceutically acceptable amounts. Preferred lactose-free dosage forms comprise an active ingredient, microcrystalline cellulose, pre-gelatinized starch, and magnesium stearate.

This invention further encompasses anhydrous pharmaceutical compositions and dosage forms which comprises an active ingredient, since water can facilitate the degradation of some compounds. For example, the addition of water (e.g., 5%) is widely accepted in the pharmaceutical arts as a means of simulating long-term storage in order to determine characteristics Such as shelf-life or the stability of formulations over time. See, e.g., Jens T. Carstensen, *Drug Stability: Principles & Practice,* 2d. Ed., Marcel Dekker, New York, N.Y., 1995, pp. 379–80. In effect, water and heat accelerate decomposition. Thus the effect of water on a formulation can be of great significance since moisture and/or humidity are commonly encountered during manufacture, handling, packaging, storage, shipment, and use of formulations.

Anhydrous pharmaceutical compositions and dosage forms of the invention can be prepared using anhydrous or low moisture containing ingredients and low moisture or low humidity conditions. Pharmaceutical compositions and dosage forms of racemic or optically pure bupropion metabolite which contain lactose are preferably anhydrous if substantial contact with moisture and/or humidity during manufacturing, packaging, and/or storage is expected.

An anhydrous pharmaceutical composition should be prepared and stored such that its anhydrous nature is maintained. Accordingly, anhydrous compositions are preferably packaged using materials known to prevent exposure to water such that they can be included in suitable formulary kits. Examples of suitable packaging include, but are not limited to, hermetically sealed foils, plastic or the like, unit dose containers, blister packs, and strip packs.

In this regard, the invention encompasses a method of preparing a solid pharmaceutical formulation which comprises an active ingredient which method comprises admixing under anhydrous or low moisture/humidity conditions the active ingredient and an excipient (e.g., lactose), wherein the ingredients are substantially free of water. The method can further comprise packaging the anhydrous or non-hygroscopic solid formulation under low moisture conditions. By using such conditions, the risk of contact with water is reduced and the degradation of the active ingredient can be prevented or substantially reduced.

Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose, and mixtures thereof.

Suitable forms of microcrystalline cellulose include, for example, the materials sold as AVICEL-PH-101, AVICEL-PH-103 AVICEL RC-581, and AVICEL-PH-105 (available from FMC Corporation, American Viscose Division, Avicel Sales, Mareus Hook, Pa., U.S.A.). An exemplary suitable binder is a mixture of microcrystalline cellulose and sodium carboxymethyl cellulose sold as AVICEL RC-581. Suitable anhydrous or low moisture excipients or additives include AVICEL-PH-103™ and Starch 1500 LM.

Examples of suitable fillers for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. The binder/filler in pharmaceutical compositions of the present invention is typically present in about 50 to about 99 weight percent of the pharmaceutical composition.

Disintegrants are used in the compositions of the invention to provide tablets that disintegrate when exposed to an aqueous environment. Too much of a disintegrant will produce tablets which may disintegrate in the bottle. Too little may be insufficient for disintegration to occur and may thus alter the rate and extent of release of the active ingredient(s) from the dosage form. Thus, a sufficient amount of disintegrant that is neither too little nor too much to detrimentally alter the release of the active ingredient(s) should be used to form the dosage forms of the compounds disclosed herein. The amount of disintegrant used varies based upon the type of formulation and mode of administration, and is readily discernible to those of ordinary skill in the art. Typically, about 0.5 to about 15 weight percent of disintegrant, preferably about 1 to about 5 weight percent of disintegrant, can be used in the pharmaceutical composition.

Disintegrants that can be used to form pharmaceutical compositions and dosage forms of the invention include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums or mixtures thereof.

Lubricants which can be used to form pharmaceutical compositions and dosage forms of the invention include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, or mixtures thereof. Additional lubricants include, for example, a syloid silica gel (AEROSIL 200, manufactured by W.R. Grace Co. of Baltimore, Md.), a coagulated aerosol of synthetic silica (marketed by Degussa Co. of Piano, Tex.), CAB-O-SIL (a pyrogenic silicon dioxide product sold by Cabot Co. of Boston, Mass.), or mixtures thereof. A lubricant can optionally be added, typically in an amount of less than about 1 weight percent of the pharmaceutical composition.

Pharmaceutical stabilizers may be used in the pharmaceutical compositions of the present invention. Acceptable stabilizers include, but are not limited to, L-cysteine hydrochloride, glycine hydrochloride, malic acid, sodium metasulfite, citric acid, tartaric acid, and L-cystine dihydrochloride. See, e.g., U.S. Pat. Nos. 5,731,000; 5,763,493; 5,541,231; and 5,358,970, all of which are incorporated herein by reference.

Dosage forms of the invention that comprise a bupropion metabolite preferably contain from about 1 mg to about 750 mg of the metabolite or a pharmaceutically acceptable salt, solvate, hydrate, or elathrate thereof. For example, each tablet, cachet, or capsule contains from about 1 mg to about 750 mg of the active ingredient. Most preferably, the tablet, cachet, or capsule contains either one of three dosages, e.g., about 25 mg, about 50 mg, or about 75 mg of a racemic or optically pure bupropion metabolite (as scored lactose-free tablets, the preferable dose form).

The invention is further defined by reference to the following examples. It will be apparent to those skilled in the art that many modifications, both to materials and methods, can be practiced without departing from the scope of this invention.

5. EXAMPLES

5.1. Example 1

Synthesis of (S,S)-Hydroxybupropion

This synthesis, which follows that depicted in Scheme 5 of the Detailed Description, comprises three steps.

Z-1-(3-Chlorophenyl)-1-tert-butyldimethylsilyloxy-1-propene: A solution of LDA (33.0 mmol) in THF (100 mL) was cooled to −78° C. and HMPA (5 mL) was added. The ketone [1-(3-chlorophenyl)-propanone] (8.6 g) in THF (20 mL) was slowly added over 45 minutes to this rapidly stirring mixture. After an additional 3 minutes at −78° C., TBSCl (33.0 mL, 1.0 M in hexane) was added. This mixture was stirred at −78° C. for 5 minutes and allowed to warm to room temperature over 40 minutes. NaHCO$_3$ (60 mL, saturated aqueous solution) was added and the mixture was extracted with CH$_2$Cl$_2$ (2×80 mL). The organic extracts were combined, washed with brine, dried over Mg$_2$SO$_4$ and concentrated to give a crude mixture. The product was purified by flash chromatography eluted with hexane/TEA (99.5/0.5), yielding 13.4 g product (Z/E ratio>99). $^1$H NMR (CDCl$_3$): δ0.12 (s, 6H), 0.95 (s, 9H), 2.75 (d, 3H), 5.25 (q, 1H), 7.2–7.42 (m, 4H).

(R)-3'-Chloro-2-hydroxyl-propiophenone: Z-1-(3'-Chlorophenyl-tert-butyldimethylsilyloxy-1-propene (12.0 g, 44 mmol) was added to a well-stirred mixture of AD-mix-β (80 g) and CH$_3$SO$_2$NH$_2$ (4.2 g, 44 mmol) in tert-butyl alcohol/water mixture (220 mL/220 mL) maintained at 0° C. The reaction mixture was stirred at 0° C. for 28 hours. Solid sodium sulfite (40 g) was added. The mixture was stirred for an additional 45 minutes and extracted with CH$_2$Cl$_2$ (2×100 mL). The combined organic extracts were washed with NaHCO$_3$ and brine, and evaporated. The residue was passed through a silica gel column to give the desired product (7.0 g). $^1$H NMR (CDCl$_3$): δ1.45 (d, 3H), 5.15 (q, 1H), 7.2–7.9 (m, 4H).

(S,S)-Iiydroxybupropion: To a solution of (R)-3'-chloro-2-hydroxyl-propiophenone (300 mg) in CH$_2$Cl$_2$ (6 mL) at −78° C. was added trifluoromethanesulfonic anhydride (0.5 g), followed by addition of 2,6-lutidine (0.26 g). The reaction mixture was allowed to warm to −40° C. and stirred at this temperature for 40 minutes. 2-Amine-2-methyl-1-propanol (0.4 g, 2.5 eq) was added, and stilTed for 2 hours at −40° C. The reaction mixture was warmed to room temperature and stirred overnight. It was extracted with CH$_2$Cl$_2$ (10 mL). The extract was washed with NaHCO$_3$, water, and brine, concentrated to give a residue. The final product was purified by chromatography eluted with CH$_3$CN (180 mg, e.e.>99%). $^1$H NMR (CDCl$_3$) δ0.78 (d, 3H), 1.1 (s, 3H), 1.4 (s, 3H), 3.2 (q, 1H), 3:4 (d, 1H), 3.8 (d, 2H), 7.2–7.65 (m, 4H). [α]=+66°(c=1, EtOH). (S,S)-hydroxybupropion free base was treated with HCl in diethyl ether to give its HCl salt. [α]=+30.6°(c=1, EtOH). $^1$H NMR (DMSO-d$_6$) δ1.0 (d, 3H), 1.32 (s, 3H), 1.56 (s, 3H), 3.4 (s, 1H), 3.4 (d, 1H), 4.0 (d, 1H), 7.5 (m, 5H), 8.8 (s, 1H), 10.1 (s, 1H). ee 99.4% as determined by HPLC with chiral column, ChiralCEl GD. 4.6×250 mm, 10 nm, hexane/ethanol/diethylamine (98:2:0.1). (R,R)-hydroxybupropion was prepared from (S)-3'-chloro-2-hydroxyl-propiophenone with 97% e.e. as determined by HPLC with chiral column, ChiralCEl GD. 4.6×250 mm, 10 nm, hexane/ethanol/diethylamine (98:2:0.1).

5.2. Example 2

Synthesis of Optically Pure Hydroxybupropion

3'-Chloro-2-bromo-propiophenone: To a solution of 3'-chloropropiophenone (50.0 g, 297 mmol) in acetonitrile (595 mL) was added bromine (16.67 mL, 327 mmol) at room temperature. The reddish-yellow solution was allowed to stir for 18 h at room temperature. The solution was concentrated in vacuo to provide a reddish solid. The crude material was dissolved in 400 mL of ethyl acetate and washed with 400 mL of water. The organic layer was dried (Na$_2$SO$_4$), filtered and concentrated in vacuo to give 72.6 g (98%) of crude product. $^1$H NMR (CDCl$_3$) δ1.90 (d, J=6 Hz, 3H), 5.21 (q, J=6 Hz, 1H), 7.37–7.88 (m, 3H), 7.98 (s, 1H).

2-Hydroxy-2-(3'-chlorophenyl)-3,5,5-trimethylmorpholine: To a solution of 3'-chloro-2-bromo-propiophenone (61.2 g, 247 mmol) in acetonitrile (752 mL) was added 2-amino-2-methyl-1-propanol (56.5 g, 630 mmol). The reaction mixture was allowed to reflux for 8 hours, then slowly cooled to room temperature. The solution was concentrated in vacuo to provide a yellow solid. The crude material was dissolved in 600 mL of ethyl acetate and washed with water (300 mL×2). The ethyl acetate layer was dried (MgSO$_4$), filtered, and concentrated in vacuo to give the product in 90% yield. $^1$H NMR (CDCl$_3$) δ0.82 (d, J=6.6 Hz, 3H), 1.07 (s, 3H), 1.39 (s, 3H), 3.19 (q, J=6.5 Hz, 1H), 3.42 (d, J=11.2 Hz, 1H), 3.83 (d, J=11.2 Hz, 2H), 7.2–7.65 (m, 4H).

(S,S)-2-Hydroxy-2-(3'-chlorophenyl)-3,5,5-trimethylmorpholine di-p-Toluoyl-L-tartaric Acid Salt: To a solution of 2-hydroxy-2-(3'-chlorophenyl-3,5,5-trimethylmorpholine (20 g, 78 mmol) in ethyl acetate (200 mL) was added 30.1 g (78 mmol) of di-p-toluoyl-L-tartaric acid. The reaction was heated to reflux for 10–30 minutes. The slurry became clear rapidly and slowly formed a precipitate. The solution was slowly cooled to room temperature over 1 hour, then filtered and washed with ethyl acetate (25 mL). The precipitate was dried under vacuum to provide 24.0 g of 2-hydroxy-2-(3'-chlorophenyl)-3,5,5-trimethylmorpholine di-p-toluoyl-L-tartaric acid salt (47% yield, 91% e.e.). The filtrate (mother liquor) was used for the preparation of (R,R)-isomer.

(R.R)-2-Hydroxy-2-(3'-chlorophenyl)-3,5,5-trimethylmorpholine di-p-Toluoyl-D-tartaric Acid Salt: To the mother liquors from above (260 mL) was added a solution of potassium carbonate (16 g, 3 equivalent) in water (60 mL) at room temperature. The reaction mixture was stirred for 5 minutes, and the organic phase was separated. The ethyl acetate layer was washed with water (30 mL), brine (40 mL), dried over MgSO$_4$, and filtered. The filtrate was added di-p-toluoyl-D-tartaric acid (15 g), heated to 75° C. for 5 minutes and cooled to room temperature for 2 hours. The precipitates were collected by filtration to give 33 g wet cake (dried to give 24 g). Enantiomeric excess of the product was determined by chiral HPLC to be 90% using a Chiralpak AD column using hexane/EtOH/DEA 85:15:01 as eluent, flow rate 1.0 ml/min. (R,R)-isomer of hydroxy bupropion is first peak (6.4 minutes, the (S,S)-isomer is second (~7.4 minutes).

Enrichment of the Diastereomeric Salt: (Same procedure for both diastereomers): To a 500 mL, round bottom flask was charged (S,S)-2-hydroxy-2-(3'-chlorophenyl-3,5,5-trimethylmorpholine di-p-toluoyl-L-tartaric acid salt (24.0 g, 37.4 mmol, 91% ee) and was added 70 mL of MeOH. The reaction was heated to reflux and to the reaction was added 90 mL of EtOAc. The reaction was heated to reflux for 20 minutes and then slowly cooled to room temperature. After stirring for 1 hour at room temperature, the reaction mixture was filtered in vacuo to provide 10.8 g of (S,S)-2-hydroxy-2-(3'-chlorophenyl-3,5,5-trimethylmorpholine di-p-toluoyl-L-tartaric acid salt (>99.9% ee). For (R,R)-2-hydroxy-2-(3'-chlorophenyl)-3,5,5-trimethylmorpholine di-p-toluoyl-D-tartaric acid salt, a total of 10.5 g, with >99.9% ee was obtained. $^1$H NMR (CDCl$_3$) δ0.86 (d, J=6.3 Hz, 3H), 1.20 (s, 3H), 1.40 (s, 3H), 2.38 (s, 3H), 3.33 (m, 1H), 3.39 (d, J=11.9 Hz, 1H), 3.97 (d, J=11.9 Hz, 1H), 5.67 (s, 2H), 7.33 (m, 4H), 7.49 (m, 4H), 7.88 (m, 4H). Optical rotation of the (R,R)-2-Hydroxy-2-(3'-chlorophenyl)-3,5,5-trimethylmorpholine di-p-toluoyl-D-tartaric acid salt: [α]$_d$=+41.88° (c=0.42, MeOH).

(2S,3S)-2-Hydroxy-2-(3'-chlorophenyl-3,5,5-trimethylmorpholine Free Base: A 500 mL RBF was charged with 10.6 g (16.5 mmol) of 2-hydroxy-2-(3'-chlorophenyl-3,5,5-trimethylmorpholine di-p-toluoyl-L-tartaric acid salt (100% ee). To the flask was added 150 mL of water, 150 mL of EtOAc, and 4.36 mL (5.0 eq) of 50% aqueous NaOH. After stirring for 1 hour at room temperature, the layers were separated. The organic layer was washed with NaHCO$_3$ (150 mL). The organic layer was dried (MgSO$_4$), concentrated in vacuo to provide 4.3 g of crude product in 100% yield. $^1$H NMR (CDCl$_3$) δ0.82 (d, J=6.6 Hz, 3H), 1.07 (s, 3H), 1.39 (s, 3H), 3.19 (q, J=6.5 Hz, 1H), 3.42 (d, J=11.2 Hz, (d, J=11.2 Hz, 2H), 7.2–7.65 (m, 4H). Free Base of the (R,R)-isomer was obtained in the same procedure. Optical rotation of the (R,R)-isomer free base: [α]$_d$=−37.7° (c=0.13, MeOH).

(2S, 3S)-2-Hydroxy-2-(3'chlorophenyl)-3,5,5-trimethylmorpholine HCl: A three-neck 250 mL RBF was charged with 4.0 g (15.68 mmol) of (2S,3S)-2-Hydroxy-2-(3'-chlorophenyl)-3,5,5-trimethylmorpholine and 100 mL of MTBE. To the reaction was slowly added 31.3 mL (31.3 mmol) of 1N HCl in ether. After stirring at room temperature for 1 hour, the white crystals were collected by filtration to provide 4.4 g (96%) of crude HCl salt. $^1$H NMR (DMSO-d$_6$) δ1.04 (d, J=6.5 Hz, 3H), 1.37 (s, 3H), 1.60 (s, 3H), 3.41 (bs, 1H), 3.52 (d, J=9.0 Hz, 1H), 4.03 (d, J=9.0 Hz, 1H), 7.61 (m, 4H), 8.90 (m, 1H), 10.41 (m, 1H). $^{13}$C NMR (DMSO) δ13.5, 20.4, 23.2, 53.0, 54.5, 65.9, 95.9, 126.1, 127.1, 129.5, 130.7, 133.5, 143.6. Optical rotation of the (S,S)-isomer HCl salt: [α]$_d$=+31.2° (c=0.64, 85% EtOH).

5.3. Example 3

Synthesis of Optically Pure Dihydrobupropion (Racemic Erythro)-Dihydrobupropion: A three-neck 1L RBF was charged with 3.0 g (10.8 mmol) of racemic bupropion. To the flask was added 30 mL of dry toluene. The suspension was cooled to −78° C. and to it was slowly added 7.2 mL (23.7 mmol) of a 3.3 M solution of Red-Al. After stirring at −78° C. for 2h, the reaction was allowed to slowly warm to 23° C. overnight. 5N NaOH was added to the reaction, and this stirred for 30 min. The layers were separated, and the organic layer was washed with water (100 mL). The organic layer was dried (MgSO$_4$) and concentrated in vacua to provide 2.6 g (86%) of crude product (Erythro:Threo ratio: 15:1).

(Racemic Erythro)-Dihydrobupropion Hydrochloride: Crude erythro dihydrobupropion (2.5 g, 10.3 mmol) was dissolved in 25 mL of methyl tert-butyl ether. The solution was stirred at 0° C. as anhydrous 2N HCl in ether (7.76 mL, 15.5 mmol) was slowly added. After stirring for 1 h at 0° C., the solid was collected by filtration, rinsed with methyl tert-butyl ether (2×5.0 mL), and dried in vacuo to provide 2.80 g of a white solid (97%). 1.0 g of the crude HCl salt was dissolved in refluxing IPA (25 mL) and slowly allowed to cool to rt. After stirring for 1 h at rt, the solids were collected by filtration to provide 0.70 g (70% recovery, >95% dr) of (+/−)-erythro dihydrobupropion HCl as a white solid. $^1$H NMR (DMSO-D$_6$) δ0.97 (d, J=6.7 Hz, 3H), 1.44 (s, 9H), 3.63 (m, 1H), 5.20 (m, 1H), 6.25 (d, J=6.2 Hz, 1H), 7.34 (m, 4H). $^{13}$C: δ12.8, 26.1, 55.4, 58.8, 71.4, 125.5, 126.5, 127.9, 130.7, 133.7, 143.8. MS m/z 241.67. Anal. Calcd for C$_{13}$H$_{20}$NOCl: C, 56.12; H, 7.61; N, 5.03. Found: C, 55.84; H, 7.67; N, 4.91.

Z-1-(3-Chlorophenyl-1-tert-butyldimetlhylsilyloxy)-1-propene: A solution of LDA (33.0 mmol) in THF (100 mL) was cooled to −78° C. and hexamethylphosphoramide (HMPA) (45 mL, about 20–25% v/v) was added. To this rapidly stirred solution was added ketone (8.6 g, 51 mmol) in 20 mL THF dropwise over 45 mm. After an additional 3 min at −78° C., TBSCl (33.0 mL) 1.0 M in hexane was added. This mixture was stirred at −78° C. for 5 min. and then allowed to warm to room temperature over 40 min. time. NaHCO$_3$ (60 mL saturated aq.) was added and the mixture was extracted with CH$_2$Cl$_2$ (80 mL×2). The organic phase was then washed with brine and dried over MgSO$_4$. The product was purified via flash chromatography eluted with Hexane/TEA (99.5/0.5) to provide 13.4 g of pure product (Z:E>99:1). $^1$H NMR (CDCL3): δ0.12 (s, 6H), 0.95 (s, 9H), 2.75 (d, 3H), 5.25 (q, 1H), 7.2–7.42 (m, 4H).

3'-Chloro-2-(R)-hydroxyl-propiophenone: To a well-stirred mixture of AD-mix-β (80 g) and CH$_3$SO$_2$NH$_2$ (4.2 g, 44 mmol) in tert-butyl alcohol/water (220 ml/220 ml) at 0° C. was added E-1-(3-chlorophenyl-1-tert-butyldimethylsilyloxy)-1-propene (12.0 g, 44 mmol). The reaction mixture was stirred at 0° C. for about 20 h. Solid sodium sulfite (40 g) was added and the mixture was stirred for an additional 45 min. CH$_2$Cl$_2$ and water was added to the reaction mixture and after separation of the layers, the aqueous phase was extracted one more time with CH$_2$Cl$_2$. The combined organic extracts were washed with NaHCO$_3$ and brine, followed by evaporation. The crude material was passed through a short column of silica gel eluted with 85% to 80% hexane/ethyl acetate to give the product (7.0 g, 98%ee). Ee was analyzed on Chiral OD column, eluted with hexane/IPA (99/1). $^1$H NMR (CDCl$_3$). $^1$H: δ1.45 (d, 3H), 5.15 (q, 1H), 7.2–7.9 (m, 4H). $^{13}$C: δ22.3, 69.7, 126.9, 128.9, 130.4. 134.1, 135.2, 135.5, 201.5. The other enantiomer of this product was prepared by replacing AD-mix-β with AD-mix-α (The product was isolated in>97% ee).

Erythro-(R,S)-Dihydrobupropion: To a solution of 3'-chloro-(R)-hydroxyl-propiophenone (4.0 g, 21.6 mmol) in CH$_2$Cl$_2$ (80 mL) at −78° C. was added trifluoromethane sulfonic anhydride (3.96 mL, 23.5 mmol), followed by addition of 2,6-lutidine (3.73 mL, 51.84 mmol). The reaction mixture was allowed to warm to −40° C. and stirred at this temperature for 40 min. Then tert-butylamine (5.66 mL, 53.8 mmol) was added and the mixture was stirred for 2 h at −40° C. The reaction mixture was warmed to 0° C. and stirred for 2 h. The reaction was quenched with NaHCO$_3$ (100 mL). The organic layer was washed with H$_2$O and brine. A 250 mL RBF was charged with the crude dichloromethane solution above. The reaction mixture was cooled to −78° C. 14.4 mL (47.52 mmol) of a 3.3 M solution of Red-Al in toluene was added dropwise at −78° C. The −78° C. solution was allowed to slowly warm to rt overnight. The reaction was quenched with 50 mL of a 5N NaOH solution at rt. The layers were separated, and the organic layer was washed with water (100 mL). The organic layer was dried (MgSO$_4$) and concentrated in vacuo to provide crude amino alcohol. The final product was purified by flash chromatography, eluted with 5–15% MeOH/EtOAc (1.93 g, 96% d.r.). $^1$H NMR (CDCl$_3$) δ0.81 (d, J=6.7 Hz, 3H), 1.22 (s, 9H), 3.15 (m, 1H), 4.63 (d, J=4.0 Hz, 1H), 7.25 (m, 4H).

(R,S)-Dihydrobupropion Hydrochloride: Crude (R,S)-Dihydrobupropion (1.85 g, 7.66 mmol) was dissolved in 18.5 mL of methyl tert-butyl ether. The solution was stirred at 0° C. as anhydrous 2N HCl in ether (5.74 mL, 11.5 mmol) was slowly added. After stirring for 1 h at 0° C., the solid was collected by filtration, rinsed with methyl tert-butyl ether (2×5.0 mL), and dried in vacua to provide 1.93 g of a white solid (90%). The crude HCl salt was dissolved in refluxing IPA (47 mL) and slowly allowed to cool to rt. After stirring for 1 h at rt, the solids were collected by filtration to provide 0.90 g (42%, 100% ee,>95% dr) of (R,S)-dihydrobupropion HCl as a white solid. $^1$H NMR (DMSO-D$_6$) δ0.97 (d, J=6.7 Hz, 3H), 1.44 (s, 9H), 3.63 (m, 1H), 5.20 (m, 1H), 6.25 (d, J=6.2 Hz, 1H), 7.34 (in, 4H). $^{13}$C: δ12.8, 26.1, 55.4, 58.8, 71.4, 125.5, 126.5, 127.9, 130.7, 133.7, 143.8. MS m/z 241.67. Anal. Calcd for C$_{13}$H$_{20}$NOCl: C, 56.12; H, 7.61; N, 5.03. Found: C, 55.84; H, 7.67; N, 4.91.

(S,R)-Dihydrobupropion: To a solution of 3'-chloro-(S)-hydroxyl-propiophenone (2.8 g, 15.2 mmol) in CH$_2$Cl$_2$(56 mL) at −78° C. was added trifluoromethane sulfonic anhydride (2.77 mL, 16.4 mmol), followed by addition of 2,6-lutidine (2.61 mL, 22.4 mmol). The reaction mixture was allowed to warm to −40° C. and stirred at this temperature for 40 min. Then tert-butylamine (3.96 mL, 37.6 mmol) was added and the mixture was stirred for 2 hrs at −40° C. The reaction mixture was warmed to 0° C. and stirred for 2 h. The reaction was quenched with $NaHCO_3$ (100 mL). The organic layer was washed with $H_2O$ and brine. A 250 mL RBF was charged with the crude dichloromethane solution above. The reaction mixture was cooled to −78° C. 10.08 mL (33.26 mmol) of a 3.3 M solution of Red-Al in toluene was added dropwise at −78° C. The −78° C. solution was allowed to slowly warm to rt overnight. The reaction was quenched with 35 mL of a 5N NaOH solution at rt. The layers were separated, and the organic layer was washed with water (100 mL). The organic layer was dried ($MgSO_4$) and concentrated in vacuo to provide crude amino alcohol. The final product was purified with chromatography, eluted with 5–15% MeOH/EtOAc (2.07 g, (S,R)-dihydrobupropion 92.3% d.r.). $^1H$ NMR ($CDCl_3$) δ0.81 (d, J=6.7 Hz, 3H), 1.22 (s, 9H), 3.15 (m, 1H), 4.63 (d, J=4.0 hz, 1H), 7.25 (m, 4H).

(S,R)-Dihydrobupropion HCl: Crude (S,R)-Dihydrobupropion (1.94 g, 8.03 mmol) was dissolved in 20 mL of methyl tert-butyl ether. The solution was stirred at 0° C. as anhydrous 2N HCl in ether (6.02 mL, 12.05 mmol) was slowly added. After stirring for 1 h at 0° C., the solid was collected by filtration, rinsed with methyl tert-butyl ether (2×5.0 mL), and dried in vacua. The solid weighed 1.85 g (88%). The crude HCl salt was dissolved in refluxing IPA (35 mL) and slowly allowed to cool to rt. After stirring for 1 h at rt, the solids were collected by filtration to provide 1.25 g (59%, 98.3% ee,>95% dr) of (S,R)-Dihydrobupropion HCl as a white solid. $^1H$ NMR (DMSO-$D_6$) δ0.97 (d, J=6.7 Hz, 3H), 1.44 (s, 9H), 3.63 (m, 1H), 5.20 (m, 1H), 6.25 (d, J=6.2 Hz, 1H), 7.34 (m, 4H). $^{13}C$: δ12.8, 26.1, 55.4, 58.8, 71.4, 125.5, 126.5, 127.9, 130.7, 133.7, 143.8. MS m/z 241.67. Anal. Calcd for $C_{13}H_{20}NOCl$: C, 56.12; H, 7.61; N, 5.03. Found: C, 55.69; H, 7.58; N, 4.73.

(Racemic Threo)-Dihydrobupropion: A three-neck 1L RBF was charged with 25.0 g (90.5 mmol) of racemic bupropion HCl. To the flask was added 333 mL of dry THF. The suspension was cooled to 0° C. and to it was slowly added 225 mL (225 mmol) of a 1M solution of borane-THF. After stinting at room temperature for 18 h, 187 mL of MeOH was added to the reaction mixture. The volatiles were removed in vacuo. To the solids were added 187 mL of 2N NaOH and the reaction was heated to 100° C. for 30 min. The solution was cooled to rt and to it was added 291 mL of 2N HCl. The reaction was stirred at rt for 30 min, then 40% $K_2CO_3$ solution was added until the solution pH is >11. The reaction mixture was extracted with 150 mL of EtOAc, dried ($MgSO_4$), and concentrated in vacuo to provide 25.2 g of crude product (85:15 d.r.).

(Racemic Threo)-Dihydrobupropion HCl: A three-neck 500 mL RBF was charged with 25.0 g (103.5 mmol) of crude racemic threo dihydrobupropion and 200 mL of MTBE. To the reaction was slowly added 62.1 mL (124.2 mmol) of 2N HCl in ether. After stirring at rt for 1 h, the white crystals were collected by filtration to provide 25.2 g (87%) of crude HCl salt. The crude HCl salt (25.2 g) was dissolved in refluxing IPA (250 mL) and slowly allowed to cool to rt. After stirring for 1 h at rt, the solids were collected by filtration to provide 17.4 g (69% recovery, 90% dr) of racemic threo dihydrobupropion HCl as a white solid. The crude HCl salt (17.4 g) was dissolved in refluxing IPA (174 mL) and slowly allowed to cool to rt. After stirring for 1 h at rt, the solids were collected by filtration to provide 13.8 g (79% recovery,>95% dr) of racemic threo dihydrobupropion HCl as a white solid.

(Racemic Threo)-Dihydrobupropion: A 500 mL RBF was charged with 12.3 g (44.24 mmol) of (racemic threo)-dihydrobupropion HCl. To the flask was added 70 mL of water, 100 rnL of EtOAc, and 30.5 g of 40% $K_2CO_3$. After stirring for 1 h at rt, the layers were separated. The organic layer was washed with $NaHCO_3$ (100 mL). The organic layer was dried ($MgSO_4$), concentrated in vacuo to provide 11.1 g (100%) of crude product. $^1H$ NMR ($CDCl_3$) δ1.05 (d, J=6.3 Hz, 3H), 1.17 (s, 9H), 2.65 (m, 1H), 3.88 (d, J=8.7 Hz, 1H), 7.26 (m, 3H), 7.41 (m, 1H); (>95% d.r.)

(R,R)-Dihydrobupropion L-Tartaric acid: A mixture of 10.6 g (43.9 mmol) of racemic threo dihydrobupropion (>95% dr) and 9.55 g (64 mmol) of L-tartaric acid in 44.63 mL of water was heated to boiling. The thick precipitate formed turned into a clear solution. The solution was slowly allowed to cool to rt and stir overnight. The solid was filtered and dried to give 7.8 g (45%) of (R,R)-Dihydrobupropion L-Tartaric acid as a white solid. Recrystallization from 23 mL of water gave 4.8 g (28%, 99.1% ee) as a white solid. $^1H$ NMR (DMSO-$D_6$) δ0.96 (d, J=6.6 Hz, 3H), 1.30 (s, 9H), 3.36 (m, 1H), 3.99 (s, 2h), 4.27 (d, J=8.7 Hz, 1H), 7.39 (m, 3H), 7.53 (s, 1H).

(R,R)-Dihydrobupropion: A 100 mL RBF was charged with 3.7 g (9.44 mmol) of (R,R)-dihydrobupropion L-tartaric acid. To the flask was added 25 mL of water, 25 mL of MTBE, and 3.78 g of 50% NaOH solution. After stirring for 1 h at rt, the layers were separated. The organic layer was washed with $NaHCO_3$ (25 mL). The organic layer was dried ($MgSO_4$), concentrated in vacuo to provide 2.1 g of crude product in 91% yield. $^1H$ NMR ($CDCl_3$) δ1.05 (d, J=6.3 Hz, 3H), 1.17 (s, 9H), 2.65 (m, 1H), 3.88 (d, J=8.7 Hz, 1H), 7.26 (m, 3H), 7.41 (m, 1H).

(R,R)-Dihydrobupropion HCl: A three-neck 100 mL RBF was charged with 2.1 g (8.69 mmol) of (R,R)-dihydrobupropion and 16.8 mL of MTBE. To the reaction was slowly added 5.2 mL (10.43 mmol) of 2N HCl in ether. After stirring at rt for 1 h, the white crystals were collected by filtration to provide 2.3 g (95%) of crude HCl salt. $^1H$ NMR. (DMSO-$D_6$) δ0.99 (d, J=6.7 Hz, 3H), 1.38 (s, 9H), 3.49 (m, 1H), 4.53 (d, J=9.0 Hz, 1H), 7.40 (m, 3H), 7.41 (m, 1H). $^{13}C$: δ17.5, 26.5, 56.3, 58.9, 74.4, 127.1, 127.9, 128.7, 130.8, 133.7, 143.9. MS m/z 241.67. Anal. Calcd for $C_{13}H_{20}NOCl$: C, 56.12; H, 7.61; N, 5.03. Found: C, 56.06; H, 7.72; N, 4.73.

(S,S)-Dihydrobupropion D-Tartaric acid: A mixture of 10.6 g (23.6 mmol) of the threo dihydrobupropion (>95% dr, recovered from the resolution of (R,R)-dihydrobupropion with L-tartaric acid) and 5.19 g (34.7 mmol) of D-tartaric acid in 23.9 mL of water was heated to boiling. The thick precipitate formed initially in the reaction turned into a clear solution. The solution was slowly allowed to cool to rt and stir overnight. The solid was filtered and dried to give 4.7 g (50%) of (S,S)-dihydrobupropion D-tartaric acid as a white solid. Recrystallization from 13.8 mL of water gave 3.4 g (36%, 100% ee) as a white solid. $^1H$ NMR (DMSO-$D_6$) δ0.96 (d, J=6.6 Hz, 3H), 1.30 (s, 9H), 3.36 (m, 1H), 3.99 (s, 2H), 4.27 (d, J=8.7 Hz, 1H), 7.39 (m, 3H), 7.53 (s, 1H).

(S,S)-Dihydrobupropion: A 100 mL RBF was charged with 2.4 g (6.12 mmol) of (S,S)dihydrobupropion D-tartaric acid. To the flask was added 16 mL of water, 16 mL of MTBE, and 2.45 g of 50% NaOH solution. After stirring for 1 h at rt, the layers wereseparated. The organic layer was washed with $NaHCO_3$ (25 mL). The organic layer was dried (MgSO$_4$), concentrated in vacuo to provide 1.3 g of crude product in 88% yield. $^1$H NMR (CDCl$_3$) δ1.05 (d, J=6.3 Hz, 3H), 1.17 (s, 9H), 2.65 (m, 1H), 3.88 (d, J=8.7 H), 7.26 (m, 3H), 7.41 (m, 1H).

(S,S)-Dihydrobupropion HCl: A three-neck 100 mL RBF was charged with 1.3 g (5.38 mmol) of (S,S)-dihydrobupropion and 10.4 mL of MTBE. To the reaction was slowly added 3.2 mL (6.45 mmol) of 2N HCl in ether. After stirring at rt for 1 h, the white crystals were collected by filtration to provide 1.32 g (89%) of crude HCl salt. $^1$H NMR (DMSO-D$_6$) δ0.99 (d, J=6.7 Hz, 3H), 1.38 (s, 9H), 3.49 (m, 1H), 4.53 (d, J=9.0 Hz, 1H), 7.40 (m, 3H), 7.41 (m, 1H). $^{13}$C: 8 17.5, 26.5, 56.3, 58.9, 74.4, 127.1, 127.9, 128.7, 130.8, 133.7, 143.9. MS m/z 241.67. Anal. Calcd for C$_{13}$H$_{20}$oNOCl: C, 56.32; H, 7.61; N, 5.03. Found: C, 55.82; H, 7.72; N, 4.82.

5.4. Example 4

Neuronal Monoamine Reuptake Inhibition

The abilities of racemic bupropion [BP(±)], and the bupropion metabolites (S,S)-hydroxybupropion [HBP(S, S)], (R,S)-hydroxybupropion [HBP(R,S)], and (S,R)-hydroxybupropion [HBP(S,R)] to inhibit the reuptake of neuronal monoamines was determined using the general methods of Moisset, B., el al., *Brain Res.* 92:157–164 (1975), Janowsky, A., et al., *J. Neurochem.* 46:1272–1276 (1986), and Perovic, S. and Muller, W. E. G., *Brain Res.* 92:157–164 (1995).

Inhibition of norepincphrinie (NE) reuptake was determined using rat hypothalamus as a tissue source and protryptiline as a reference compound. Inhibition of dopamine (DA) reuptake was determined using rat corpora striata as a tissue source and GBR 12909 as a reference compound. Inhibition of serotonin (5-HT) reuptake was determined using rat brain as a tissue source and imipramine as a reference compound. The specific conditions for each assay are shown in Table 1:

TABLE 1

| Assay | Substrate | Incubation | Detection Method |
|---|---|---|---|
| NE | [$^3$H]NE (0.2 µCi/mL) | 20 min./37° C. | liquid scintillation |
| DA | [$^3$H]DA (0.2 µCi/mL) | 15 min./37° C. | liquid scintillation |
| 5-HT | [$^3$H]5-HT (0.2 µCi/mL) | 15 min./37° C. | liquid scintillation | wherein the end products observed were formed by the incorporation of [$^3$H]NE, [$^3$H]DA, and [$^3$H]5-HT into synaptosomes. Radioactivity was determined with a scintillation counter (Topcount, Packard) using a liquid scintillation cocktail (Microscint 0, Packard).

Raceinic bupropion and the bupropion metabolites were first tested in each assay at 10 µM in duplicate or triplicate. For assays wherein they inhibited the reuptake by more than 50% at this concentration, they were further tested at eight concentrations in duplicate to obtain full inhibition curves. In each experiment, the respective reference compound was tested at eight concentrations in duplicate to obtain an inhibition curve in order to validate this experiment.

IC$_{50}$ values and Hill coefficients (nH) were determined for the reference compounds and the test compounds (i.e., bupropion and metabolites of bupropion) by non-linear regression analysis of their inhibition curves. These parameters were obtained by Hill equation curve fitting.

None of the compounds tested significantly inhibited 5-HT reuptake. The IC$_{50}$ values determined for these compounds with regard to norepinephrine and dopamine reuptake are presented in Table 2:

TABLE 2

| | NE reuptake | | DA reuptake | |
|---|---|---|---|---|
| Compounds | IC$_{50}$ (nM) | (nH) | IC$_{50}$ (nM) | (nH) |
| HBP(S, S) | 229 | (0.8) | 1,400 | (1.0) |
| HBP(RS, RS) | 756 | (1.1) | | |
| BP(±) | 746 | (>3) | 294 | (0.9) |
| HBP(R, R) | — | | — | |
| | IC$_{50}$(nM) | (nH) | IC$_{50}$(nM) | (nH) |
| protriptyline | 3.6/3.8 | (2.6)/(1.4) | | |
| GBR 12909 | | | 5.6 | (1.7) |

The measured biological activity of the optically pure bupropion metabolites is unexpectedly different from the activity of bupropion itself. For example, racemic bupropion (i.e., (±)1-(3-chlorophenyl)-2-[(1,1-dimethylethyl)amino]-1-propanone) inhibits norepinephrine uptake with an IC$_{50}$ of approximately 746 nM, while the optically pure metabolite (S,S)-hydroxybupropion (i.e., (S,S)-2-(3-chlorophenyl)-2-hydroxy-3,5,5-trimethyl-moipholinol) inhibits norepinephrine with a dramatically lower IC$_{50}$ of 229 nM. And while racemic bupropion inhibits dopamine uptake with an IC$_{50}$ of approximately 294 nM, the optically pure metabolite (S,S)-2-(3-chlorophenyl)-2-hydroxy-3,5,5-trimethyl-morpholinol does not significantly inhibit dopamine uptake, having an IC$_{50}$ of approximately 1400 nM. But like racemic bupropion, this optically pure metabolite does not measurably inhibit serotonin uptake.

These results indicate that the biological activity of each of the bupropion metabolites of the invention is dramatically and unexpectedly different from that of bupropion. These results further indicate that bupropion metabolites are superior in their abilities to treat certain disorders. For example, optically pure (S,S)-hydroxybupropion is surprisingly selective with regard to its inhibition of neuronal monoamine reuptake, and may thus be used to inhibit norepinephrine reuptake.

5.5. Example 5

In Vivo Activity: Seizure Model

The pharmacological effects of a bupropion metabolite in whole animals can be determined in a number of ways. For example, its ability to inhibit artificially induced seizures in mice may be informative.

Using the methods of Green and Murray, *J. Pharm. Plarmacol.* 41:879–880 (1989), a group of 4–6 rats is lightly restrained and a 10 mg/mL solution of the convulsant drug pentetrazol is infused via a 25 gauge needle inserted into a tail vein of each rat at a rate of 2.6 mL/min. The time of infusion of the convulsant drug required to produce the first myoclonic twitch (which occurs with the first EEG abnormality) is recorded and doses required to produce the seizure calculated. Seizure threshold is expressed as mg/kg and can be calculated using the formula:

$$(I \times C \times T)/(60 \times W)$$

wherein I is the infusion rate measured in mL per minute; C is the drug concentration in 10 mg/mL; T is the time to twitch in seconds; and W is the rate weight in kilograms.

Bupropion metabolites are administered by intraperitoneal or intravenous injection 15 minutes before the determination of seizure threshold.

5.6. Example 6

In Vivo Activity Phenylquinone Writhing Assay

The pharmacological effects of a bupropion metabolite can also be determined from the antiphenylquinone writhing test, which is a standard procedure for detecting and comparing analgesic activity in laboratory animals. The advantage of this test is that it generally correlates well with human efficacy. In response to an injected, locally irritating solution, the animals have writhings that are inhibited by analgesic agents.

Mice dosed with at least two dose levels of a bupropion metabolite are challenged with phenyl-p-benzoquinone (PPQ) given intraperitoneally and then observed for the characteristic stretch-writhing syndrome. Lack of writhing constitutes a positive response. The degree of analgesic protection can be calculated on the basis of suppression of writhing relative to control animals run on the same day. Time response data are also obtained. Observations are made early enough after dosing to detect differences in onset.

For example, the following protocols may be used, wherein ten mice are used per dose group:

Preparation of Phenylquinone: PPQ is made-up as a 0.02% aqueous solution in ethyl alcohol. PPQ (20 mg) is ground and dissolved in a tissue homogenizer in 5 mL ethyl alcohol, and the volume brought to 100 mL with distilled water, preheated to 45° C. The resulting solution should be a clear amber color. PPQ solutions are made fresh twice daily and, if necessary, about every four hours because of the tendency of PPQ to precipitate out of solution.

Dose amounts: 0.1, 0.3, 1.0, 3.0, 10.0, 30.0, and 100.0 mg/kg.

Positive Control: Aspirin—200 mg/kg.

Writhing: PPQ solution is administered intraperitoneally using a 25 gauge, ⅝" long needle on a 1 mL syringe. Each animal in the group receives 0.25 mL. The group of ten mice per dose level is observed closely for ten minutes for exhibition of writhing. The stability of the PPQ solution(s) to produce the writhing response is verified for each preparation in ten mice to which the vehicle was administered prior to PPQ administration.

Characteristic patterns of writhing consist of torsion of the abdomen and thorax, drawing the hind legs close to the body and raising the heels of the hind feet off of the floor.

Observation Times: Reference and positive control article activity is studied at 60 minutes after administration. After the designated absorption time interval of a group has elapsed, the mice are challenged with PPQ. Each mouse receives one dose of 0.25 mL of PPQ. After PPQ administration, the mouse is placed in individual Plexiglas® squares 4"×4"×5" deep and observed closely for a ten minute period for exhibition of the writhing syndrome.

Scoring Determinations: The total number of writhes for each mouse is recorded. The mean number of writhes for the control and each positive control and reference group is compared and percent inhibition calculated.

5.7. Example 7

In Vivo Activity: Formalin Test

The pharmacological effects of a bupropion metabolite may also be determined from other models, some of which are discussed by Bannon, A. W., el al., *Science* 279:77–81 (1998). One of these models is the formalin test.

The formalin test is an animal model for persistent inflammatory pain. In the formalin test, the second phase of the biphasic nociceptive response is thought to be mediated in part by a sensitization of neuronial function at the level of the spinal cord, and reflect the clinical observation of hyperalgesia associated with tissue injury.

Using the method of Dubusson, D., and Dennis, S. G., *Science* 4:161 (1977), rats are allowed to acclimate to their individual cages for 20 minutes, after which time 50 mL of a 5% formalin solution is injected into the dorsal aspect of one of the rear paws. The rats are then returned to the clear observation cages, which are suspended above mirror panels. Only phase 2 of the formalin test may be scored, and phase 2 may be defined as the 20-minute period of time from 30 to 50 minutes after formalin injection. The investigator records nocifensive behaviors in the injected paw of four animals during the session by observing each animal for one 15-second observation period during each 1-minute interval. Nocifensive behaviors include flinching, licking, or biting the injected paw. In dose-response studies, the test compound (or saline) is administered 5 minutes before the injection of formalin. In antagonist studies, the antagonists or saline are administered 10 minutes before treatment.

5.8. Example 8

In vivo Activity: Neuropathic Pain Model

Another pharmacological model discussed by Bannon, A. W., et al., *Science* 279:77–81(1998) is the neuropathic pain test. In the neuropathic pain model, nerve injury results in neuroplastic changes that lead to allodynia, a condition characterized by nocifensive behavioral responses to what are normally non-noxious stimuli conducted by $A\beta$ fibers. In the Chung model of neuropatlic pain, allodynia is produced in the hind limb ipsilateral by ligation of the LS and L6 spinal nerves. S. H. Kim and J. M. Chung, *Science* 50, 355 (1992). According to this model, a within-subjects design in which all animals receive all treatments is used for dose-response studies.

Using the Chung model, baseline allodynia scores are determined for all animals before the start of the drug studies. Only rats with threshold scores are considered allodynic and used in further testing. Drug studies (separate studies for each compound) begin approximately 2 weeks after nerve ligation surgery. For dose-response experiments, animals are tested over a 2-week period. Test days are separated by 2 to 3 day intervals during which no testing is conducted and no treatment is given. On test days, animals are placed in individual chambers and allowed to acclimate for 15 to 20 minutes. After acclimation, baseline scores are determined. Next, animals are treated and scores are determined 15, 30, 50, and 120 minutes after treatment. This procedure is repeated on test days until each animal has received all treatments for any given drug. The treatment order is counterbalanced across animals. For statistical analysis, the time point of peak effect is compared.

5.9. Example 9

Oral Formulation

Table 3 provides the ingredients for a lactose-free tablet dosage form of a bupropion metabolite:

TABLE 3

| Component | Quantity per Tablet (mg) |
| --- | --- |
| Bupropion metabolite (e.g., (S,S)-hydroxybupropion) | 75 |
| Microcrystalline cellulose | 125 |
| Talc | 5.0 |
| Water (per thousand tablets) | 30.0 mL* |
| Magnesium Stearate | 0.5 |

*The water evaporates during manufacture.

The active ingredient (bupropion metabolite) is blended with the cellulose until a uniform blend is formed. The smaller quantity of corn starch is blended with a suitable quantity of water to form a corn starch paste. This is then mixed with the uniform blend until a uniform wet mass is formed. The remaining corn starch is added to the resulting wet mass and mixed until uniform granules are obtained. The granules are then screened through a suitable milling machine, using a ¼ inch stainless steel screen. The milled granules are then dried in a suitable drying oven until the desired moisture content is obtained. The dried granules are then milled through a suitable milling machine using ¼ mesh stainless steel screen. The magnesium stearate is then blended and the resulting mixture is compressed into tablets of desired shape, thickness, hardness and disintegration. Tablets are coated by standard aqueous or nonaqueous techniques.

Another tablet dosage formulation suitable for use with the active ingredients of the invention is provided by Table 4:

TABLE 4

| | Quantity per Tablet (mg) | | |
| --- | --- | --- | --- |
| Component | Formula A | Formula B | Formula C |
| Bupropion metabolite (e.g., (S,S)-hydroxybupropion) | 20 | 40 | 100 |
| Microcrystalline cellulose | 134.5 | 114.5 | 309.0 |
| Starch BP | 30 | 30 | 60 |
| Pregelatinized Maize Starch BP | 15 | 15 | 30 |
| Magnesium Stearate | 0.5 | 0.5 | 1.0 |
| Compression Weight | 200 | 200 | 500 |

The active ingredient is sieved and blended with cellulose, starch, and pregelatinized maize starch. Suitable volumes of purified water are added and the powders are granulated. After drying, the granules are screened and blended with the magnesium stearate. The granules are then compressed into tablets using punches.

Tablets of other strengths may be prepared by altering the ratio of active ingredient to pharmaceutically acceptable carrier, the compression weight, or by usinig different punches.

5.10. Example 10

Oral Formulation

Table 5 provides the ingredients for a capsule dosage form of a bupropion metabolite:

TABLE 5

| | Quantity per Tablet (mg) | | |
| --- | --- | --- | --- |
| Component | Formula A | Formula B | Formula C |
| Bupropion metabolite (e.g., (S,S)-hydroxybupropion) | 25 | 50 | 75 |
| Microcrystalline cellulose | 149.5 | 124.5 | 374 |
| Corn Starch | 25 | 25 | 50 |
| Water (per thousand tablets) | 0.5 | 0.5 | 1.0 |
| Magnesium Stearate | 200 | 200 | 200 |

The active ingredient, cellulose, and corn starch are blended until uniform; then the magnesium stearate is blended into the resulting powder. The resulting mixture is encapsulated into suitably sized two-piece hard gelatin capsules using suitable machinery. Other doses can be prepared by altering the ratio of active ingredient to pharmaceutically acceptable carrier, the fill weight, and, if necessary, by changing the capsule size to suit.

The active ingredient, cellulose, and corn starch are blended until uniform; then the magnesium stearate is blended into the resulting powder. The resulting mixture is encapsulated into suitably sized two-piece hard gelatin capsules using suitable machinery. Other doses can be prepared by altering the ratio of active ingredient to pharmaceutically acceptable carrier, the fill weight, and, if necessary, by changing the capsule size to suit.

The embodiments of the invention described above are intended to be merely exemplary and those skilled in the art will recognize, or be able to ascertain using no more than routine experimentation, numerous equivalents to the specific procedures described herein. All such equivalents are considered to be within the scope of the invention and are encompassed by the following claims.

What is claimed is:

1. A method of treating or preventing sexual dysfunction which comprises administering to a patient in need of such treatment or prevention a therapeutically or prophylactically effective amount of a bupropion metabolite, or a pharmaceutically acceptable salt, solvate, hydrate, or clathrate thereof, wherein the bupropion metabolite is 2-(3-chlorophenyl)-2-hydroxy-3,5,5-trimethyl-morpholinol, 1-(3-chlorophenyl)-2-[(1,1-dimethylethanol)amino]-1-propanol, and 1-(3-chlorophenyl)-2-[(1,1-dimethylethanol)amino]-1-propanone.

2. The method of claim 1 wherein the patient is male.

3. The method of claim 2 wherein the sexual dysfunction is erectile dysfunction.

4. The method of claim 1 wherein the patient is female.

5. The method of claim 1 wherein the bupropion metabolite is optically pure.

6. The method of claim 1 wherein the optically pure bupropion metabolite is (R,R)-2-(3-chlorophenyl)-2-hydroxy-3,5,5-trimethyl-morpholinol; (S,S)-2-(3-chlorophenyl)-2-hydroxy-3,5,5-trimethyl-morpholinol; (R,R)-2-(tert-butylamino)-1-(3-chlorophenyl)-propane-1-ol; (S,R)-2-(tert-butylamino)-1-(3-chlorophenyl)-propan-1-ol; (S,S )-2-(tert-butylamino)-1-(3-chlorophenyl)-propan-1-ol; (R,S)-2-(tert-butylamino)-1-(3-chlorophenyl)-propan-1-ol; (R)-1-(3-chlorophenyl)-2-[(1,1-dimethylethanol)amino]-1-propanone; and (S)-1-(3-chlorophenyl)-2-[(1,1-dimethylethanol)amino]-1-propanone.

7. The method of claim 6 wherein the optically pure bupropion metabolite is optically pure (S,S)-2-(3-chlorophenyl)-2-hydroxy-3,5,5-trimethyl-morpholinol.

8. The method of claim 1 wherein the bupropion metabolite, or pharmaceutically acceptable salt, solvate, hydrate, or clathrate thereof, is administered orally, transdermally, or mucosally.

9. The method of claim 1 wherein the bupropion metabolite, or pharmaceutically acceptable salt, solvate, hydrate, or clathrate thereof, is adjunctively administered with a 5-HT$_3$ antagonist.

10. The method of claim 9 wherein the 5-HT$_3$ antagonist is an antiemetic agent.

11. The method of claim 10 wherein the 5-HT$_3$ antagonist is selected from the group consisting of granisetron, metoclopramide, ondansetron, renzapride, zacopride, norcisapride, tropisetron, and optically pure stereoisomers, active metabolites, and pharmaceutically acceptable salts, hydrates, solvates, hydrates, and clathrates thereof.

12. A method of treating or preventing erectile dysfunction, which comprises administering to a patient in need of such treatment or prevention a therapeutically or prophylactically effective amount of a bupropion metabolite, or a pharmnaceutically acceptable salt, solvate, hydrate, or clathrate thereof, wherein the bupropion metabolite is 2-(3-chlorophenyl)-2-hydroxy-3,5,5-trimethyl-morpholinol, 1-(3-chlorophenyl)-2-[(1,1-dimethylethanol)amino]-1-propanol, and 1-(3-chlorophenyl)-2-[(1,1-dimethylethanol)amino]-1-propanone.

13. The method of claim 12, wherein the bupropion metabolite is optically pure.

14. The method of claim 13, wherein the optically pure bupropion metabolite is (R,R)-2-(3-chlorophenyl)-2-hydroxy-3,5,5-trimethyl-morpholinol; (S,S)-2-(3-chlorophenyl)-2-hydroxy-3,5,5-trimethyl-morpholinol; (R,R)-2-(tert-butylamino)-1-(3-chlorophenyl)-propan-1-ol; (S,R)-2-(tert-butylamino)-1-(3-chlorophenyl)-propan-1-ol; (S,S)-2-(tert-butylamino)-1-(3-chlorophenyl)-propan-1-ol; (R,S)-2-(tert-butylamino)-1-(3-chlorophenyl)-propan-1-ol; (R)-1-(3-chlorophenyl)-2-[(1,1-dimethylethanol)amino]-1-propanone; or (S)-1-(3-chlorophenyl)-2-[(1,1-dimethylethanol)amino]-1-propanone.

15. The method of claim 14, wherein the optically pure bupropion metabolite is optically pure (S,S)-2-(3-chlorophenyl)-2-hydroxy-3,5,5-trimethyl-morpholinol.

16. The method of claim 12, wherein the bupropion metabolite, or pharmaceutically acceptable salt, solvate, hydrate, or clathrate thereof, is administered orally, transdermally, or mucosally.

17. The method of claim 12, wherein the bupropion metabolite, or pharmaceutically acceptable salt, solvate, hydrate, or clathrate thereof, is adjunctively administered with a 5-HT3 antagonist.

18. The method of claim 17, wherein the 5-HT3 antagonist is an antiemetic agent.

19. The method of claim 18, wherein the 5-HT3 antagonist is granisetron, metoclopramide, ondansetron, renzapride, zacopride, norcisapride, tropisetron, or optically pure stereoisomers, active metabolites, or pharmaceutically acceptable salts, hydrates, solvates, hydrates, or clathrates thereof.

20. A method of treating or preventing premature ejaculation, which comprises administering to a patient in need of such treatment or prevention a therapeutically or prophylactically effective amount of a bupropion metabolite, or a pharmaceutically acceptable salt, solvate, hydrate, or clathrate thereof, wherein the bupropion metabolite is 2-(3-chlorophenyl)-2-hydroxy-3,5,5-trimethyl-morpholinol, 1-(3-chlorophenyl)-2-[(1,1dimethylethanol)amino]-1-propanol, and 1-(3-chlorophenyl)-2-[(1,1-dimethylethanol)amino]-1-propanone.

21. The method of claim 20, wherein the bupropion metabolite is optically pure.

22. The method of claim 21, wherein the optically pure bupropion metabolite is (R,R)-2-(3-chlorophenyl)-2-hydroxy-3,5,5-trimethyl-morpholinol; (S,S)-2-(3-chlorophenyl)-2- hydroxy-3,5,5-trimethyl-morpholinol; (R,R)-2-(tert-butylamino)-1-(3-chlorophenyl)-propan-1-ol; (S,R)-2-(tert-butylamino)-1-(3-chlorophenyl)-propan-1-ol: (S,S)-2-(tert-butylamino)-1-(3-chlorophenyl)-propan-1-ol; (R,S)-2-(tert-butylamino)-1-(3-chlorophenyl)-propan-1-ol; (R)-1-(3-chlorophenyl)-2-[(1,1-dimethylethanol)amino]-1-propanone; or (S)-1-(3-chlorophenyl)-2-[(1,1-dimethylethanol)amino]-1-propanone.

23. The method of claim 22, wherein the optically pure bupropion metabolite is optically pure (S,S)-2-(3-chlorophenyl)-2-hydroxy-3,5,5-trimethyl-morpholinol.

24. The method of claim 20, wherein the bupropion metabolite, or pharmaceutically acceptable salt, solvate, hydrate, or clathrate thereof, is administered orally, transdermally, or mucosally.

25. The method of claim 20, wherein the bupropion metabolite, or pharmaceutically acceptable salt, solvate, hydrate, or clathrate thereof, is adjunctively administered with a 5-HT3 antagonist.

26. The method of claim 25, wherein the 5-HT3 antagonist is an antiemetic agent.

27. The method of claim 26, wherein the 5-HT3 antagonist is granisetron, metoclopramide, ondansetron, renzapride, zacopride, norcisapride, tropisetron, and optically pure stereoisomers, active metabolites, or pharmaceutically acceptable salts, hydrates, solvates, hydrates, or clathrates thereof.

28. A method of treating or preventing vaginal dryness, which comprises administering to a patient in need of such treatment or prevention a therapeutically or prophylactically effective amount of a bupropion metabolite, or a pharmaceutically acceptable salt, solvate, hydrate, or clathrate thereof, wherein the bupropion metabolite is 2-(3-chlorophenyl)-2-hydroxy-3,5,5-trimethyl-morpholinol, 1-(3-chlorophenyl)-2-[(1,1-dimethylethanol)amino]-1-propanol, and 1-(3-chlorophenyl)-2-[(1,1-dimethylethanol)amino]-1-propanone.

29. The method of claim 28, wherein the bupropion metabolite is optically pure.

30. The method of claim 29, wherein the optically pure bupropion metabolite is (R,R)-2-(3-chlorophenyl)-2-hydroxy-3,5,5-trimethyl-morpholinol; (S,S)-2-(3-chlorophenyl)-2-hydroxy-3,5,5-trimethyl-morpholinol; (R,R)-2-(tert-butylamino)-1-(3-chlorophenyl)-propan-1-ol; (S,R)-2-(tert-butylamino)-1-(3-chlorophenyl)-propan-1-ol; (S,S)-2-(tert-butylamino)-1-(3-chlorophenyl)-propan-1-ol; (R,S)-2-(tert-butylamino)-1-(3-chlorophenyl)-propan-1-ol; (R)-1-(3-chlorophenyl)-2-[(1,1-dimethylethanol)amino]-1-propanone; or (S)-1-(3-chlorophenyl)-2-[(1,1-dimethylethanol)amino]-1-propanone.

31. The method of claim 30, wherein the optically pure bupropion metabolite is optically pure (S,S)-2-(3-chlorophenyl)-2-hydroxy-3,5,5-trimethyl-morpholinol.

32. The method of claim 28, wherein the bupropion metabolite, or pharmaceutically acceptable salt, solvate, hydrate, or clathrate thereof, is administered orally, transdermally, or mucosally.

33. The method of claim 28, wherein the bupropion metabolite, or pharmaceutically acceptable salt, solvate, hydrate, or clathrate thereof, is adjunctively administered with a 5-HT3 antagonist.

34. The method of claim 33, wherein the 5-HT3 antagonist is an antiemetic agent.

35. The method of claim 33, wherein the 5-HT3 antagonist is granisetron, metoclopramide, ondansetron, renzapride, zacopride, norcisapride, tropisetron, or optically pure stereoisomers, active metabolites, or pharmaceutically acceptable salts, hydrates, solvates, hydrates, or clathrates thereof.

36. A method of treating or preventing vaginismus, which comprises administering to a patient in need of such treatment or prevention a therapeutically or prophylactically effective amount of a bupropion metabolite, or a pharmaceutically acceptable salt, solvate, hydrate, or clathrate thereof, wherein the bupropion metabolite is 2-(3-chlorophenyl)-2-hydroxy-3,5,5-trimethyl-morpholinol, 1-(3-chlorophenyl)-2-[(1,1-dimethylethanol)amino]-1-propanol, and 1-(3-chlorophenyl)-2-[(1,1-dimethylethanol)amino]-1-propanone.

37. The method of claim 36, wherein the bupropion metabolite is optically pure.

38. The method of claim 37, wherein the optically pure bupropion metabolite is (R,R)-2-(3-chlorophenyl)-2-hydroxy-3,5,5-trimethyl-morpholinol; (S,S)-2-(3-chlorophenyl)-2-hydroxy-3,5,5-trimethyl-morpholinol; (R,R)-2-(tert-butylamino)-1-(3-chlorophenyl)-propan-1-ol; (S,R)-2-(tert-butylamino)-1-(3-chlorophenyl)-propan-1-ol; (S,S)-2-(tert-butylamino)-1-(3-chlorophenyl)-propan-1-ol; (R,S)-2-(tert-butylamino)-1-(3-chlorophenyl)-propan-1-ol; (R)-1-(3-chlorophenyl)-2-[(1,1-dimethylethanol)amino]-1-propanone; or (S)-1-(3-chlorophenyl)-2-[(1,1-dimethylethanol)amino]-1-propanone.

39. The method of claim 37, wherein the optically pure bupropion metabolite is optically pure (S,S)-2-(3-chlorophenyl)-2-hydroxy-3,5,5-trimethyl-morpholinol.

40. The method of claim 36, wherein the bupropion metabolite, or pharmaceutically acceptable salt, solvate, hydrate, or clathrate thereof, is administered orally, transdermally, or mucosally.

41. The method of claim 36, wherein the bupropion metabolite, or pharmaceutically acceptable salt, solvate, hydrate, or clathrate thereof, is adjunctively administered with a 5-HT3 antagonist.

42. The method of claim 41, wherein the 5-HT3 antagonist is an antiemetic agent.

43. The method of claim 41, wherein the 5-HT3 antagonist is granisetron, metoclopramide, ondansetron, renzapride, zacopride, norcisapride, tropisetron, or optically pure stereoisomers, active metabolites, or pharmaceutically acceptable salts, hydrates, solvates, hydrates, or clathrates thereof.

44. A method of treating or preventing decreased libido, which comprises administering to a patient in need of such treatment or prevention a therapeutically or prophylactically effective amount of a bupropion metabolite, or a pharmaceutically acceptable salt, solvate, hydrate, or clathrate thereof, wherein the bupropion metabolite is 2-(3-chlorophenyl)-2-hydroxy-3,5,5-trimethyl-morpholinol, 1-(3-chlorophenyl)-2-[(1,1-dimethylethanol)amino]-1-propanol, and 1-(3-chlorophenyl)-2-[(1,1-dimethylethanol)amino]-1-propanone.

45. The method of claim 44, wherein the patient is male.
46. The method of claim 44, wherein the patient is female.
47. The method of claim 44, wherein the bupropion metabolite is optically pure.

48. The method of claim 47, wherein the optically pure bupropion metabolite is (R,R)-2-(3-chlorophenyl)-2-hydroxy-3,5,5-trimethyl-morpholinol; (S,S)-2-(3-chlorophenyl)-2-hydroxy-3,5,5-trimethyl-morpholinol; (R,R)-2-(tert-butylamino)-1-(3-chlorophenyl)-propan-1-ol; (S,R)-2-(tert-butylamino)-1-(3-chlorophenyl)-propan-1-ol; (S,S)-2-(tert-butylamino)-1-(3-chlorophenyl)-propan-1-ol; (R,S)-2-(tert-butylamino)-1-(3-chlorophenyl)-propan-1-ol; (R)-1-(3-chlorophenyl)-2-[(1,1-dimethylethanol)amino]-1-propanone; and (S)-1-(3-chlorophenyl)-2-[(1,1-dimethylethanol)amino]-1-propanone.

49. The method of claim 47, wherein the optically pure bupropion metabolite is optically pure (S,S)-2-(3-chlorophenyl)-2-hydroxy-3,5,5-trimethyl-morpholinol.

50. The method of claim 44, wherein the bupropion metabolite, or pharmaceutically acceptable salt, solvate, hydrate, or clathrate thereof, is administered orally, transdermally, or mucosally.

51. The method of claim 44, wherein the bupropion metabolite, or pharmaceutically acceptable salt, solvate, hydrate, or clathrate thereof, is adjunctively administered with a 5-HT3 antagonist.

52. The method of claim 51, wherein the 5-HT3 antagonist is an antiemetic agent.

53. The method of claim 51, wherein the 5-HT3 antagonist is granisetron, metoclopramide, ondansetron, renzapride, zacopride, norcisapride, tropisetron, or optically pure stereoisomers, active metabolites, or pharmaceutically acceptable salts, hydrates, solvates, hydrates, or clathrates thereof.

54. A method of treating or preventing lack of sexual excitement, which comprises administering to a patient in need of such treatment or prevention a therapeutically or prophylactically effective amount of a bupropion metabolite, or a pharmaceutically acceptable salt, solvate, hydrate, or clathrate thereof, wherein the bupropion metabolite is 2-(3-chlorophenyl)-2-hydroxy-3,5,5-trimethyl-morpholinol, 1-(3-chlorophenyl)-2-[(1,1-dimethylethanol)amino]-1-propanol, and 1-(3-chlorophenyl)-2-[(1,1-dimethylethanol)amino]-1-propanone.

55. The method of claim 54, wherein the patient is male.
56. The method of claim 54, wherein the patient is female.
57. The method of claim 54, wherein the bupropion metabolite is optically pure.

58. The method of claim 57, wherein the optically pure bupropion metabolite is (R,R)-2-(3-chlorophenyl)-2-hydroxy-3,5,5-trimethyl-morpholinol; (S,S)-2-(3-chlorophenyl)-2-hydroxy-3,5,5-trimethyl-morpholinol; (R,R)-2-(tert-butylamino)-1-(3-chlorophenyl)-propan-1-ol; (S,R)-2-(tert-butylamino)-1-(3-chlorophenyl)-propan-1-ol; (S,S)-2-(tert-butylamino)-1-(3-chlorophenyl)-propan-1-ol; (R,S)-2-(tert-butylamino)-1-(3-chlorophenyl)-propan-1-ol; (R)-1-(3-chlorophenyl)-2-[(1,1-dimethylethanol)amino]-1-propanone; and (S)-1-(3-chlorophenyl)-2-[(1,1-dimethylethanol)amino]-1-propanone.

59. The method of claim 57, wherein the optically pure bupropion metabolite is optically pure (S,S)-2-(3-chlorophenyl)-2-hydroxy-3,5,5-trimethyl-morpholinol.

60. The method of claim 54, wherein the bupropion metabolite, or pharmaceutically acceptable salt, solvate, hydrate, or clathrate thereof, is administered orally, transdermally, or mucosally.

61. The method of claim 54, wherein the bupropion metabolite, or pharmaceutically acceptable salt, solvate, hydrate, or clathrate thereof, is adjunctively administered with a 5-HT3 antagonist.

62. The method of claim 61, wherein the 5-HT3 antagonist is an antiemetic agent.

63. The method of claim 61, wherein the 5-HT3 antagonist is granisetron, metoclopramide, ondansetron, renzapride, zacopride, norcisapride, tropisetron, or optically pure stereoisomers, active metabolites, or pharmaceutically acceptable salts, hydrates, solvates, hydrates, or clathrates thereof.

64. A method of treating or preventing anorgasmia, which comprises administering to a patient in need of such treatment or prevention a therapeutically or prophylactically effective amount of a bupropion metabolite, or a pharmaceutically acceptable salt, solvate, hydrate, or clathrate thereof, wherein the bupropion metabolite is 2-(3-chlorophenyl)-2-hydroxy-3,5,5-trimethyl-morpholinol, 1-(3-chlorophenyl)-2-[(1,1-dimethylethanol)amino]-1-propanol, and 1-(3-chlorophenyl)-2-[(1,1-dimethylethanol)amino]-1-propanone.

65. The method of claim 64, wherein the patient is male.

66. The method of claim 64, wherein the patient is female.

67. The method of claim 64, wherein the bupropion metabolite is optically pure.

68. The method of claim 67, wherein the optically pure bupropion metabolite is (R,R)-2-(3-chlorophenyl)-2-hydroxy-3,5,5-trimethyl-morpholinol; (S,S)-2-(3-chlorophenyl)-2-hydroxy-3,5,5-trimethyl-morpholinol; (R,R)-2-(tert-butylamino)-1-(3-chlorophenyl)-propan-1-ol; (S,R)-2-(tert-butylamino)-1-(3-chlorophenyl)-propan-1-ol; (S,S)-2-(tert-butylamino)-1-(3-chlorophenyl)-propan-1-ol; (R,S)-2-(tert-butylamino)-1-(3-chlorophenyl)-propan-1-ol; (R)-1-(3-chlorophenyl)-2-[(1,1-dimethylethanol)amino]-1-propanone; and (S)-1-(3-chlorophenyl)-2-[(1,1-dimethylethanol)amino]-1-propanone.

69. The method of claim 67, wherein the optically pure bupropion metabolite is optically pure (S,S)-2-(3-chlorophenyl)-2-hydroxy-3,5,5-trimethyl-morpholinol.

70. The method of claim 64, wherein the bupropion metabolite, or pharmaceutically acceptable salt, solvate, hydrate, or clathrate thereof, is administered orally, transdermally, or mucosally.

71. The method of claim 64, wherein the bupropion metabolite, or pharmaceutically acceptable salt, solvate, hydrate, or clathrate thereof, is adjunctively administered with a 5-HT3 antagonist.

72. The method of claim 71, wherein the 5-HT3 antagonist is an antiemetic agent.

73. The method of claim 71, wherein the 5-HT3 antagonist is granisetron, metoclopramide, ondansetron, renzapride, zacopride, norcisapride, tropisetron, or optically pure stereoisomers, active metabolites, or pharmaceutically acceptable salts, hydrates, solvates, hydrates, or clathrates thereof.

74. A method of treating or preventing inability to obtain orgasm, which comprises administering to a patient in need of such treatment or prevention a therapeutically or prophylactically effective amount of a bupropion metabolite, or a pharmaceutically acceptable salt, solvate, hydrate, or clathrate thereof, wherein the bupropion metabolite is 2-(3-chlorophenyl)-2-hydroxy-3,5,5-trimethyl-morpholinol, 1-(3-chlorophenyl)-2-[(1,1-dimethylethanol)amino]-1-propanol, and 1-(3-chlorophenyl)-2-[(1,1-dimethylethanol)amino]-1-propanone.

75. The method of claim 74, wherein the patient is male.

76. The method of claim 74, wherein the patient is female.

77. The method of claim 74, wherein the bupropion metabolite is optically pure.

78. The method of claim 77, wherein the optically pure bupropion metabolite is (R,R)-2-(3-chlorophenyl)-2-hydroxy-3,5,5-trimethyl-morpholinol; (S,S)-2-(3-chlorophenyl)-2-hydroxy-3,5,5-trimethyl-morpholinol; (R,R)-2-(tert-butylamino)-1-(3-chlorophenyl)-propan-1-ol; (S,R)-2-(tert-butylamino)-1-(3-chlorophenyl)-propan-1-ol; (S,S)-2-(tert-butylamino)-1-(3-chlorophenyl)-propan-1-ol; (R,S)-2-(tert-butylamino)-1-(3-chlorophenyl)-propan-1-ol; (R)-1-(3-chlorophenyl)-2-[(1,1-dimethylethanol)amino]-1-propanone; and (S)-1-(3-chlorophenyl)-2-[(1,1-dimethylethanol)amino]-1-propanone.

79. The method of claim 77, wherein the optically pure bupropion metabolite is optically pure (S,S)-2-(3-chlorophenyl)-2-hydroxy-3,5,5-trimethyl-morpholinol.

80. The method of claim 74, wherein the bupropion metabolite, or pharmaceutically acceptable salt, solvate, hydrate, or clathrate thereof, is administered orally, transdermally, or mucosally.

81. The method of claim 74, wherein the bupropion metabolite, or pharmaceutically acceptable salt, solvate, hydrate, or clathrate thereof, is adjunctively administered with a 5-HT3 antagonist.

82. The method of claim 81, wherein the 5-HT3 antagonist is an antiemetic agent.

83. The method of claim 81, wherein the 5-HT3 antagonist is granisetron, metoclopramide, ondansetron, renzapride, zacopride, norcisapride, tropisetron, or optically pure stereoisomers, active metabolites, or pharmaceutically acceptable salts, hydrates, solvates, hydrates, or clathrates thereof.

84. A method of treating or preventing psycho-sexual dysfunction, which comprises administering to a patient in need of such treatment or prevention a therapeutically or prophylactically effective amount of a bupropion metabolite, or a pharmaceutically acceptable salt, solvate, hydrate, or clathrate thereof, wherein the bupropion metabolite is 2-(3-chlorophenyl)-2-hydroxy-3,5,5-trimethyl-morpholinol, 1-(3-chlorophenyl)-2-[(1,1-dimethylethanol)amino]-1-propanol, and 1-(3-chlorophenyl)-2-[(1,1-dimethylethanol)amino]-1-propanone.

85. The method of claim 84, wherein the psycho-sexual dysfunction is inhibited sexual desire, inhibited sexual excitement, inhibited female orgasm, inhibited male orgasm, premature ejaculation, functional dyspareunia, functional vaginismus, or atypical psychosexual dysfunction.

86. The method of claim 84, wherein the patient is male.

87. The method of claim 84, wherein the patient is female.

88. The method of claim 84, wherein the bupropion metabolite is optically pure.

89. The method of claim 88, wherein the optically pure bupropion metabolite is (R,R)-2-(3-chlorophenyl)-2-hydroxy-3,5,5-trimethyl-morpholinol; (S,S)-2-(3-chlorophenyl)-2-hydroxy-3,5,5-trimethyl-morpholinol; (R,R)-2-(tert-butylamino)-1-(3-chlorophenyl)-propan-1-ol; (S,R)-2-(tert-butylamino)-1-(3-chlorophenyl)-propan-1-ol; (S,S)-2-(tert-butylamino)-1-(3-chlorophenyl)-propan-1-ol; (R,S)-2-(tert-butylamino)-1 -(3-chlorophenyl)-propan-1-ol; (R)-1-(3-chlorophenyl)-2-[(1,1-dimethylethanol)amino]-1-propanone; and (S)-1-(3-chlorophenyl)-2-[(1,1-dimethylethanol)amino]-1-propanone.

90. The method of claim 88, wherein the optically pure bupropion metabolite is optically pure (S,S)-2-(3-chlorophenyl)-2-hydroxy-3,5,5-trimethyl-morpholinol.

91. The method of claim 84, wherein the bupropion metabolite, or pharmaceutically acceptable salt, solvate, hydrate, or clathrate thereof, is administered orally, transdermally, or mucosally.

92. The method of claim 84, wherein the bupropion metabolite, or pharmaceutically acceptable salt, solvate, hydrate, or clathrate thereof, is adjunctively administered with a 5-HT3 antagonist.

93. The method of claim 92, wherein the 5-HT3 antagonist is an antiemetic agent.

94. The method of claim 92, wherein the 5-HT3 antagonist is granisetron, metoclopramide, ondansetron, renzapride, zacopride, norcisapride, tropisetron, or optically pure stereoisomers, active metabolites, or pharmaceutically acceptable salts, hydrates, solvates, hydrates, or clathrates thereof.

* * * * *